United States Patent
Reichert et al.

(10) Patent No.: US 11,406,582 B2
(45) Date of Patent: Aug. 9, 2022

(54) AGENT FOR OXIDATIVE LIGHTENING AND BLEACHING OF THE HAIR

(71) Applicant: Henkel AG & Co. KGaA, Duesseldorf (DE)

(72) Inventors: Anja Reichert, Duesseldorf (DE); Oliver Nemitz, Duesseldorf (DE); Juergen Schoepgens, Schwalmtal (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 184 days.

(21) Appl. No.: 16/934,272

(22) Filed: Jul. 21, 2020

(65) Prior Publication Data
US 2021/0022979 A1 Jan. 28, 2021

(30) Foreign Application Priority Data
Jul. 23, 2019 (DE) ..................... 10 2019 210 907.1

(51) Int. Cl.
| | |
|---|---|
| A61K 8/58 | (2006.01) |
| A61K 8/81 | (2006.01) |
| A61K 8/06 | (2006.01) |
| A61K 8/34 | (2006.01) |
| A61Q 5/08 | (2006.01) |
| A61K 8/22 | (2006.01) |

(52) U.S. Cl.
CPC ............ *A61K 8/585* (2013.01); *A61K 8/064* (2013.01); *A61K 8/22* (2013.01); *A61K 8/345* (2013.01); *A61K 8/8147* (2013.01); *A61Q 5/08* (2013.01); *A61K 2800/10* (2013.01); *A61K 2800/882* (2013.01)

(58) Field of Classification Search
CPC ......... A61K 8/81; A61K 8/8147; A61Q 19/10
IPC .................................. A61Q 5/08; A61K 8/585
See application file for complete search history.

(56) References Cited

U.S. PATENT DOCUMENTS

| | | | |
|---|---|---|---|
| 9,592,185 B2 | 3/2017 | Klug et al. | |
| 10,143,634 B2 | 12/2018 | Witte et al. | |
| 2018/0168941 A1 | 6/2018 | Schoepgens et al. | |
| 2019/0183750 A1 | 6/2019 | Schoepgens et al. | |
| 2021/0259934 A1 | 8/2021 | Rohland et al. | |

FOREIGN PATENT DOCUMENTS

| | | |
|---|---|---|
| DE | 102010054866 A1 | 8/2011 |
| DE | 102014226540 A1 | 6/2016 |
| DE | 102018209891 A1 | 12/2019 |
| FR | 3060309 A1 | 6/2018 |
| FR | 3060310 A1 | 6/2018 |
| FR | 3060311 A1 | 6/2018 |
| FR | 3060371 A1 | 6/2018 |
| FR | 3060372 A1 | 6/2018 |
| FR | 3060373 A1 | 6/2018 |

*Primary Examiner* — Walter E Webb
(74) *Attorney, Agent, or Firm* — Lorenz & Kopf, LLP

(57) ABSTRACT

The object of the present disclosure are agents for oxidative hair bleaching with a pH value in the range from about 10.0 to about 11.0, containing from about 70-95% by weight of water, an alkalizing agent, from about 0.1-2% by weight of anionic, zwitterionic or amphoteric surfactant, from about 0.1-1.5% by weight of sodium polyacrylate, wherein only small amounts, if any, of linear saturated alkanols having two or three hydroxy groups and from 2 to 8 carbon atoms in the alkyl group are included. Furthermore, no saturated and unsaturated non-alkoxylated alkanols having one hydroxy group and from 1 to 50 carbon atoms in the alk(en)yl group, no saturated and unsaturated alkanecarboxylic acids with 1 to 50 carbon atoms, no crosslinked copolymer built up from acrylic acid and non-ethoxylated esters of acrylic acid with linear C10-C30 monoalcohols as monomers and no oxidizing agents are contained.

20 Claims, No Drawings

AGENT FOR OXIDATIVE LIGHTENING AND BLEACHING OF THE HAIR

CROSS-REFERENCE TO RELATED APPLICATION

This application claims priority to German Patent Application No. 10 2019 210 907.1, filed Jul. 23, 2019, which is incorporated herein by reference in its entirety.

TECHNICAL FIELD

The present application concerns a product for the oxidative lightening and bleaching of hair, a kit comprising that hair-lightening product and a hair-lightening process using that hair-lightening product.

BACKGROUND

In addition to colouring, the lightening of one's own hair colour or bleaching is a wish of many consumers, as a blonde hair colour is regarded as attractive and desirable in terms of fashion. If hair is to be lightened or even bleached, the natural colourants responsible for the natural colour of the hair, especially the body's own melanin eumelanin and phaeomelanin, are broken down oxidatively using oxidizing agents, such as hydrogen peroxide in particular, and the hair is thus decolourized and lightened or even bleached.

To develop an optimal brightening performance of the oxidant, oxidative brightening agents require an alkaline pH value for reaction acceleration, especially in the range of about pH 10.0 to about 11.0. However, hydrogen peroxide, the oxidizing agent most commonly used for cosmetic purposes, can only be stored at low pH values, i.e. in the range of about pH 2.0 to about 6.5. Therefore, commercially available bleaching agents are usually packaged as a kit including an aqueous hydrogen peroxide solution with a more acidic pH value, preferably in the range of about pH 2.0 to about 6.5, and an alkalizing component. Both components are only mixed together shortly before application to the hair. Both components are matched to each other in their composition so that the resulting application mixture has an alkaline pH value, especially in the range of about pH 9 to about 10. In addition, a persulphate and/or percarbonate containing composition—usually anhydrous—can be added to the alkaline hydrogen peroxide-containing application mixture shortly before application to the hair to enhance the lightening effect of the bleaching agent. Such a commercial bleaching agent is available as a kit including an aqueous hydrogen peroxide solution with a more acidic pH value, preferably in the range of about pH 2.0 to about 6.5, an alkalizing component—often in cream form—and an anhydrous composition containing persulphate and/or percarbonate. Often the kits described above also contain one or more portions of a hair conditioner for the nourishing after-treatment of the hair after the completed bleaching treatment.

The application time for attractive whitening results is usually in the range of from about 5 to about 60 minutes. It is therefore necessary that the individual components of the ready-to-use bleaching agent are formulated in such a way that on the one hand they can be mixed well with each other and then distributed on the hair to be bleached and on the other hand they are sufficiently viscous to remain on the hair to be bleached during the application time without dripping down. This viscosity can be adjusted by polymeric thickeners in the ready-to-use whitening or bleaching agent, whereby this thickener can be contained both in the alkalizing component and in the oxidizing agent preparation as well as in the optional anhydrous—persulphate and/or percarbonate-containing composition.

The alkaline pH value of the alkalizing component is adjusted with alkalizing agents such as alkanolamines, ammonia, basic amino acids or inorganic bases and mixtures of these alkalizing agents.

To produce the ready-to-use bleaching agent, the alkalizing component is usually mixed with an aqueous hydrogen peroxide solution to form a homogeneous cream or gel and applied directly afterwards to the hair to be lightened. Optionally, an anhydrous persulphate and/or percarbonate containing composition can be added to this mixture, which further enhances the brightening and bleaching performance of the agent. This bleaching agent remains on the hair for a period of from about 5 to about 60 minutes until the oxidative breakdown of the natural melanin hair dyes, i.e. eumelanin and phaeomelanin, is complete. The bleaching agent is then washed out of the hair. The degree of melanin degradation and thus the achieved lightening of the hair depends on various properties of the hair, in particular on the original amount of the black-brown pigment eumelanin and the red-gold pigment phaeomelanin as well as on the structure of the hair fibres.

The alkalizing agent or mixture of alkalizing agents is usually incorporated into a cosmetically suitable carrier, such as a cream or gel. The carrier ensures a homogeneous distribution and a sufficient residence time of the hair whitening agent on the hair.

A disadvantage is the complex production of such a cream. A lot of energy is required to melt the fat components and emulsify them. The subsequent cooling process consumes large amounts of cooling water.

A further disadvantage is that a cream has to be packed relatively elaborately. Due to their higher viscosity, creams are not free-flowing and cannot be transferred from a storage bottle into the application bottle, in which the hydrogen peroxide solution is already present, by simply tipping it over. Instead, the alkaline whitening creams are mainly packed in flexible aluminum tubes, a packaging material with high energy and raw material consumption.

A higher viscosity of the whitening creams may still be disadvantageous with regard to the production of the application mixture. For this purpose, the alkaline whitening cream is mixed by hand with the developer preparation. For a good whitening result you need a homogeneous application mixture. It must be possible to produce this as quickly as possible because the activation and decomposition of the hydrogen peroxide begins on contact with the alkalizing agent. The easiest way to achieve the fastest possible mixing is to make the whitening cream and developer preparation as liquid as possible. On the other hand, the application mixture itself should have a higher viscosity so that it remains on the hair and does not drip down.

The present disclosure was based on the task of providing an oxidative brightening or bleaching agent which can be produced under the most economical and sustainable conditions. Furthermore, the present disclosure was based on the task of providing an oxidative brightening or bleaching agent which can be packaged under the most economical and sustainable conditions. Furthermore, the present disclosure was based on the task of providing an oxidative brightening or bleaching agent which is easy to mix and apply.

BRIEF SUMMARY

Agents, kits-of-parts, and methods for lightening or bleaching hair are provided. In an exemplary embodiment, an agent includes about 70 to 95 weight percent water, an alkalizing agent, and a surfactant. The surfactant is selected from anionic, zwitterionic and amphoteric surfactants, and is present in an amount of about 0.1 to 2 weight percent. Sodium polyacrylate is also present in an amount of about 0.1 to 1.5 weight percent, where the sodium polyacrylate has mass-average molar mass of from about 1,000,000 to about 20,000,000 Daltons. The agent also includes a linear saturated alkanol in an amount of about 0 to about 3 weight percent. The agent does include any of (1) a crosslinked copolymer formed from acrylic acid and non-ethoxylated esters of acrylic acid with linear C10-C30 monoalcohols as monomers, (2) saturated or unsaturated non-alkoxylated alkanols having a hydroxy group and 1 to 50 carbon atoms in the alk(en)yl group, (3) saturated or unsaturated alkanecarboxylic acids with 1 to 50 carbon atoms, and (4) oxidizing agents. The agent has a pH of from about 10 to about 11.

A kit of parts is also described in an alternate embodiment. The kit of parts includes the agent described above in a container (C1), and a container (C2) containing an oxidizing agent preparation (M2). The oxidizing agent preparation (M2) includes about 40 to about 96% by weight water, hydrogen peroxide in a total amount of from about 0.5 to about 23% by weight, and has a pH value in the range from about 2.0 to about 6.5.

A method of lightening or bleaching hair is described in yet another embodiment. The method includes providing an agent (M1) as described above and an oxidizing agent (M2) including water at about 40 to 96 weight percent, hydrogen peroxide at about 0.5 to 23 weight percent, and having a pH from about 2.0 to 6.5. Agent (M1) and oxidizing agent (M2) are mixed together to form a mixture in a ration (M1):(M2) of from about 1:0.8 to about 1:2.5. The mixture is applied to hair and left on the hair for about 1 to about 60 minutes. The hair is then rinsed with water or a cleansing product.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The tasks mentioned above are solved by an agent for oxidative hair whitening, which contains the following, based on its weight:
from about 70-95% by weight water,
at least one alkalizing agent,
at least one surfactant selected from anionic, zwitterionic and amphoteric surfactants and mixtures thereof in a total amount of from about 0.1-2% by weight,
Sodium polyacrylate in a total amount of from about 0.1-1.5% by weight, preferably from about 0.5-1.3% by weight, particularly preferably from about 0.8-1.1% by weight, preferably with a mass-average molar mass Mw in the range from about 1,000,000 to about 20,000,000 Daltons, preferably from about 6,000,000 to about 15,000,000 Daltons,
at least one linear saturated alkanol with two or three hydroxy groups and 2 to 8 carbon atoms in the alkyl group in a total amount of from about 0-3% by weight,
where
no crosslinked copolymer composed of acrylic acid and non-ethoxylated esters of acrylic acid with linear C10-C30 monoalcohols as monomers,
no saturated and unsaturated non-alkoxylated alkanols having a hydroxy group and 1 to 50 carbon atoms in the alk(en)yl group,
no saturated and unsaturated alkanecarboxylic acids with 1 to 50 carbon atoms and
no oxidizing agents
are contained,
exemplified in that the agent has a pH value in the range from about 10.0 to about 11.0, preferably in the range from about 10.1 to about 10.8, each measured at about 20° C.

The agent as contemplated herein represents the alkalizing component of an oxidative hair brightening or bleaching agent. This is usually mixed with an aqueous hydrogen peroxide preparation immediately before use and then applied to the hair to be lightened. Until mixed with the aqueous hydrogen peroxide preparation, the agent of the present disclosure contains no oxidizing agents. Optionally, an anhydrous persulphate and/or percarbonate-containing composition can be added to the mixture of the agent as contemplated herein or the agent preferred as contemplated herein and an aqueous hydrogen peroxide preparation, thereby further enhancing the whitening and bleaching performance of the agent.

Water Content

The agent as contemplated herein contains, in each case based on its weight, from about 70-95% by weight of water, preferably from about 78-91% by weight of water.

Alkalizing Agent

The agent as contemplated herein contains at least one alkalizing agent. The alkalizing agent preferred for adjusting the preferred pH value as contemplated herein is selected from the group comprising ammonium hydroxide, basic amino acids, alkali metal hydroxides, alkanolamines, alkali metal silicates, alkali metal phosphates and alkali metal hydrogen phosphates and mixtures thereof. The preferred alkali metal ions are lithium, sodium, and potassium, especially sodium or potassium.

The basic amino acids which can be used as alkalizing agents are preferably selected from the group L-arginine, D-arginine, D,L-arginine, L-lysine, D-lysine, and D,L-lysine, particularly preferably L-arginine, D-arginine, and D,L-arginine as an alkalizing agent as contemplated herein.

The alkali metal hydroxides which can be used as alkalizing agents are preferably selected from sodium hydroxide and potassium hydroxide.

The alkanolamines which can be used as alkalizing agents are preferably selected from primary amines with a C2-C6 alkyl base body which carries at least one hydroxyl group. Particularly preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-Aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, and 2-amino-2-methylpropan-1,3-diol. Alkanolamines particularly preferred as contemplated herein are selected from the group 2-aminoethan-1-ol, 2-amino-2-methylpropan-1-ol and 2-amino-2-methyl-propan-1,3-diol.

A particularly preferred alkalizing agent as contemplated herein is monoethanolamine (2-aminoethan-1-ol). To achieve a whitening process which is as odourless as possible, monoethanolamine is preferably contained in a total amount of from about 0.1-10% by weight, preferably from about 0.5-9% by weight, further preferably from about 1 to about 8% by weight, particularly preferably from about 2 to about 7% by weight, extremely preferably from about 3-6% by weight and further extremely preferably from about 4-5% by weight—based on the weight of the hair whitening or bleaching agent as contemplated herein.

In addition to or instead of monoethanolamine, other preferred hair brightening or bleaching agents as contemplated herein contain ammonium hydroxide, i.e. ammonia in the form of its aqueous solution. The corresponding aqueous ammonia solutions can be from about 10 to about 35 percent solutions (calculated in volume %. about 100 g aqueous ammonia solution with about 25% by volume NH3 contains about 50 g ammonia. Preferably, ammonia is used in the form of a from about 20 to about 30 volume percent solution, especially preferred in the form of about a 25-volume percent solution.

In a particularly preferred version, the hair whitening or bleaching agent as contemplated herein contains ammonium hydroxide in an amount of from about 0.1-6% by weight, preferably from about 0.5-5% by weight, more preferably from about 1 to about 4% by weight, particularly preferably from about 1.5 to about 3% by weight, extremely preferably from about 2-2.5% by weight, based on the weight of the hair whitening or bleaching agent as contemplated herein.

Furthermore, other alkalizing agents such as potassium hydroxide and sodium hydroxide may be included, preferably in a total amount of from about 0.05-1.5% by weight, particularly preferably from about 0.1-0.6% by weight, in each case based on the weight of the hair whitening or bleaching agent as contemplated herein.

In another particularly preferred form, the hair whitening or bleaching agent as contemplated herein contains at least one alkalizing agent selected from ammonium hydroxide, basic amino acids, alkali metal hydroxides, alkanolamines, alkali metal silicates, alkali metal phosphates and alkali metal hydrogen phosphates and mixtures thereof, in a total amount of from about 2-10% by weight, preferably from about 3-9% by weight, particularly preferably from about 4-8% by weight, extremely preferably from about 4.5-7% by weight, based on the weight of the hair brightening or bleaching agent as contemplated herein.

In another particularly preferred form, the hair whitening or bleaching agent as contemplated herein contains at least one alkalizing agent in a total amount of from about 0.02-0.4 mol/100 g, preferably from about 0.05-0.2 mol/100 g, particularly preferably from about 0.08-0.17 mol/100 g, extremely preferably from about 0.1-0.13 mol/100 g selected from ammonium hydroxide, basic amino acids, alkali metal hydroxides, alkanolamines, alkali metal silicates, alkali metal phosphates and alkali metal hydrogen phosphates and mixtures thereof, each in moles of alkalizing agent per about 100 grams of the composition of the present disclosure.

The hair brightening or bleaching agents as contemplated herein are further exemplified by a pH value in the range from about 10.0 to about 11.0, preferably in the range from about 10.1 to about 10.8, particularly preferably from about 10.3-10.5, each measured at about 20° C.

Anionic, Zwitterionic or Amphoteric Surfactant

The composition as contemplated herein contains, based on its weight, at least one surfactant selected from anionic, zwitterionic and amphoteric surfactants and mixtures thereof in a total amount of from about 0.1-2% by weight, preferably from about 0.3-1.5% by weight, and particularly preferably from about 0.5-1.2% by weight, each based on the weight of the composition.

For the purposes of the present application, surfactants and emulsifiers are amphiphilic (bifunctional) compounds which include at least one hydrophobic and at least one hydrophilic part of the molecule.

For the purposes of the present application, saturated and unsaturated alkane-1-ols with at least 4 carbon atoms in the alk(en)yl radical, alkanecarboxylic acids with at least 4 carbon atoms in the alk(en)yl radical and glyceryl fatty acid mono- and diesters with at least 4 carbon atoms in the fatty acid radical are not counted as surfactants.

The hydrophobic radical is preferably a hydrocarbon chain with 8-30 carbon atoms, which can be saturated or unsaturated, linear or branched. This $C_8$-$C_{30}$-Alkyl chain is particularly preferably linear. The basic properties of the surfactants and emulsifiers are oriented adsorption at interfaces as well as aggregation to micelles and the formation of lyotropic phases.

When selecting surfactants suitable as contemplated herein, it may be preferable to use a mixture of surfactants in order to optimally adjust the properties of the whitening or bleaching agents as contemplated herein.

Suitable anionic surfactants for the agents as contemplated herein are all anionic surfactants suitable for use on the human body, which have a water-solubilizing anionic group, for example a sulphate, sulfonate or phosphate group, and a lipophilic alkyl group with about 8 to 30 carbon atoms, preferably 8 to 24 carbon atoms in the molecule, with the exception of linear and branched fatty acids with 8 to 30 carbon atoms and their salts (Soaps). In addition, glycol or polyglycol ether groups, ester, ether and amide and hydroxyl groups may also be present in the molecule. Examples of suitable anionic surfactants are, in each case in the form of the sodium, potassium and ammonium and the mono-, di- and trialkanolammonium salts with 2 to 4 carbon atoms in the alkanol group, polyethoxylated ether carboxylic acids, acyl sarcosides, acyl taurides, acyl isethionates, sulphosuccinic acid mono- and dialkyl esters and sulphosuccinic acid mono-alkyl polyoxyethyl esters with 1 to 6 ethylene oxide groups, linear alkane sulfonates, linear alpha-olefin sulfonates, sulfonates of unsaturated fatty acids with up to 6 double bonds, alpha-sulfo fatty acid methyl esters of fatty acids, $C_8$-$C_{20}$-Alkyl sulphates and $C_8$-$C_{20}$-Alkyl ether sulphates with 1 to 15 oxyethyl groups, mixtures of surface-active hydroxy sulfonates, sulphated hydroxyalkyl polyethylene and/or hydroxyalkylene propylene glycol ethers, esters of tartaric acid or citric acid with ethoxylated or propoxylated fatty alcohols, optionally polyethoxylated alkyl and/or alkenyl ether phosphates, sulphated fatty acid alkylene glycol esters and mono glyceride sulphates and monoglyceride ether sulphates. Preferred anionic surfactants are selected from $C_8$-$C_{20}$-alkyl sulphates, $C_8$-$C_{20}$-alkyl ether sulphates and $C_8$-$C_{20}$-ether carboxylic acids, each with 8 to 20 C atoms in the alkyl group and 0 to 12 ethylene oxide groups in the molecule. Sodium laureth (2) sulphate is particularly preferred.

Zwitterionic surfactants are those surface-active compounds which carry a lipophilic alkyl group with about 8 to 30 C atoms, preferably 8 to 24 C atoms and at least one quaternary ammonium group and at least one carboxylate, sulfonate or sulphate group. Particularly suitable zwitterionic surfactants are the so-called betaines such as the N-alkyl-N, N-dimethylammonium glycinate, for example cocoalkyldimethylammonium glycinate, N-acylaminopropyl-N, N-dimethylammonium glycinate, for example cocoacylaminopropyl-dimethylammonium glycinate (with the INCI name Cocamidine), and 2-alkyl-3-carboxymethyl-3-hydroxyethyl-imidazolines each having 8 to 18 carbon atoms in the alkyl or acyl group and cocoacylaminoethyl-hydroxyethylcarboxymethylglycinate. A preferred zwitterionic surfactant is the cocoacylaminopropyldimethylammonium glycinate known under the INCI designation cocamidopropyl betaine.

Amphoteric surfactants are surface-active compounds which contain a $C_8$-$C_{30}$-alkyl- or -acyl group and at least one free amino group and at least one —COOH— or —$SO_3H$— group in the molecule and are capable of forming internal salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with 8 to 30 C atoms in the alkyl group. Particularly preferred amphoteric surfactants are N-Cocoalkylaminopropionate, Cocoacylaminoethylaminopropionate and $C_{12}$-$C_{18}$ Acylsarcosine.

Anionic or zwitterionic surfactants preferred as contemplated herein are selected from $C_8$-$C_{20}$-alkyl sulphates, $C_8$-$C_{20}$-alkyl ether sulphates and $C_8$-$C_{20}$-ether carboxylic acids, each with 8 to 20 C atoms in the alkyl group and 0 to 12 ethylene oxide groups in the molecule, sodium laureth (2) sulphate is particularly preferred, furthermore from cocoacylaminopropyldimethylammonium glycinate and from mixtures of these surfactants.

Agents which are extraordinarily preferred as contemplated herein contain at least one anionic or zwitterionic surfactant selected from $C_8$-$C_{20}$ alkyl sulphate, $C_8$-$C_{20}$ alkyl ether sulphates and $C_8$-$C_{20}$-ether carboxylic acids, in each case having 8 to 20 C atoms in the alkyl group and 0 to 12 ethylene oxide groups in the molecule, sodium laureth(2) sulphate being particularly preferred, further including cocoacylaminopropyl dimethylammonium glycinate and mixtures of these surfactants, in a total amount of from about 0.1-2% by weight, preferably from about 0.3-1.5 wt. %, and particularly preferably from about 0.5-1.2 wt. %, each based on the weight of the agent.

A further essential feature of the hair brightening or bleaching agents as contemplated herein is a content of sodium polyacrylate in a total amount of from about 0.1-1.5% by weight, preferably from about 0.5-1.3% by weight, particularly preferably from about 0.8-1.1% by weight, in each case based on the weight of the hair brightening or bleaching agent.

As contemplated herein, sodium polyacrylate is preferably understood to mean polymers with the CAS number 9003-04-7. Sodium polyacrylates preferred as contemplated herein have a weight-average molecular weight Mw in the range from about 1,000,000 to about 20,000,000 Daltons, preferably from about 6,000,000 to about 15,000,000 Daltons. The average molecular weight Mw can be determined for example by gel permeation chromatography (GPC) with polystyrene as the internal standard in accordance with DIN 55672-3, Version August 2007.

The sodium polyacrylate leads to a further thickening of the hair whitening or bleaching agent, while at the same time giving it the consistency of a creamy gel.

Hair whitening or bleaching agents preferred as contemplated herein contain sodium polyacrylate in a total amount of from about 0.5-1.3% by weight, particularly preferably from about 0.8-1.1% by weight, each based on the weight of the agent.

In a preferred embodiment, the sodium polyacrylate is contained as sodium polyacrylate pre-gelled in a water-in-oil emulsion. Here it is particularly preferred that the sodium polyacrylate-containing water-in-oil emulsion contains, in each case based on its weight, from about 40-60% by weight of sodium polyacrylate, a total of from about 25-45% by weight of oil(s), a total of from about 0.5-4.9% by weight of surfactant(s) and from about 0.5-4.9% by weight of water.

The oil contained in the water-in-oil emulsion containing sodium polyacrylate is particularly preferably selected from natural and synthetic hydrocarbons, particularly preferably from mineral oil, paraffin oils, $C_{18}$-$C_{30}$-isoparaffins, in particular isoeicosane, polyisobutenes and polydecenes, $C_8$-$C_{16}$-isoparaffins, as well as 1,3-di-(2-ethylhexyl) cyclohexane; the benzoic acid esters of linear or branched $C_{8-22}$-alkanols; triglycerides of linear or branched, saturated or unsaturated, optionally hydroxylated $C_{8-30}$-fatty acids, in particular natural oils; the dicarboxylic acid esters of linear or branched $C_2$-$C_{10}$-alkanols; the esters of linear or branched saturated or unsaturated fatty alcohols with 2-30 carbon atoms with linear or branched saturated or unsaturated fatty acids with 2-30 carbon atoms, which may be hydroxylated; the adducts of 1 to 5 propylene oxide units with mono- or polyvalent $C_{8-22}$-alkanols; the $C_8$-$C_{22}$-fatty alcohol esters of monovalent or polyvalent $C_2$-$C_7$-hydroxycarboxylic acids; the symmetrical, asymmetrical or cyclic esters of carbonic acid with $C_{3-22}$-alkanols, $C_{3-22}$-alkandioles or $C_{3-22}$-alkantrioles; the esters of dimers of unsaturated $C_{12}$-$C_{22}$-fatty acids (dimer fatty acids) with monovalent linear, branched or cyclic $C_2$-$C_{18}$-alkanols or with polyvalent linear or branched $C_2$-$C_6$-alkanols; Silicone oils and mixtures of the aforementioned substances. A particularly preferred oil as contemplated herein is mineral oil.

The surfactant contained in the water-in-oil emulsion containing sodium polyacrylate is particularly preferably selected from non-ionic surfactants. Non-ionic surfactants used with particular preference are selected from 7-80 moles of ethylene oxide per mole of ethoxylated castor oil, ethoxylated $C_8$-$C_{24}$-alkanols with 5-30 moles of ethylene oxide per mole, ethoxylated $C_8$-$C_{24}$-carboxylic acids with 5-30 moles of ethylene oxide per mole, with 4-50 moles of ethylene oxide per mole of ethoxylated sorbitan monoesters of linear saturated and unsaturated $C_{12}$-$C_{30}$-carboxylic acids, which can be hydroxylated, especially those of myristic acid, palmitic acid, stearic acid or of mixtures of these fatty acids, alkyl mono- and oligoglycosides with 8 to 22 carbon atoms in the alkyl radical and their ethoxylated analogues, and mixtures of the aforementioned substances.

The ethoxylated $C_8$-$C_{24}$-alkanols have the formula $R^1O(CH_2CH_2O)_nH$, where $R^1$ stands for a linear or branched alkyl and/or alkenyl radical with 8-24 carbon atoms and n, the average number of ethylene oxide units per molecule, for numbers from 5-30, preferably 6-20, particularly preferably 6 to 12 moles of ethylene oxide to 1 mole of alkanol, which is preferably selected from caprylic alcohol, 2-Ethylhexyl alcohol, capric alcohol, lauryl alcohol, isotridecyl alcohol, tridecyl alcohol, myristyl alcohol, cetyl alcohol, palmitoleyl alcohol, stearyl alcohol, isost, Oleyl alcohol, elaidyl alcohol, petroselinyl alcohol, arachyl alcohol, gadoleyl alcohol, behenyl alcohol, erucyl alcohol and brassidyl alcohol and from their technical mixtures. Also adducts of 10-100 moles of ethylene oxide with technical fatty alcohols with 12-18 carbon atoms, such as coconut, palm, palm kernel or tallow fatty alcohol, are also suitable. Trideceth-6, Isotrideceth-6, Undeceth-6, Myreth-6, Laureth-10, Laureth-12, Laureth-15, Laureth-20, Laureth-30, Myreth-10, Myreth-12, Myreth-15, Myreth-20, Myreth-30, Ceteth-10, Ceteth-12, Ceteth-15, Ceteth-20, Ceteth-30, Steareth-10, Steareth-12, Steareth-15, Steareth-20, Steareth-30, Oleth-10, Oleth-12, Oleth-15, Oleth-20, Oleth-30, Ceteareth-10, Ceteareth-12, Ceteareth-15, Ceteareth-20, Ceteareth-30 and Coceth-10, Coceth-12, Coceth-15, Coceth-20 and Coceth-30; trideceth-6 and isotrideceth-6 and mixtures thereof are particularly preferred.

The ethoxylated $C_8$-$C_{30}$-Carboxylic acids have the formula $R^1O(CH_2CH_2O)_nH$, where $R^1O$ stands for a linear or branched saturated or unsaturated acyl radical with 8-30 carbon atoms and n, the average number of ethylene oxide units per molecule, for numbers of 5-30, preferably 6-20, particularly preferably 6 to 12 moles of ethylene oxide with 1 mole of $C_8$-$C_{30}$-Carboxylic acid, which is preferably selected from caprylic acid, 2-Ethylhexanoic acid, capric acid, lauric acid, isotridecanoic acid, myristic acid, cetylic acid, palmitoleic acid, stearic acid, isostearic acid, Oleic acid, elaidic acid, petroselinic acid, arachyic acid, gadoleic acid, behenic acid, erucic acid and brassidic acid and from their technical mixtures. Adducts of 5-30, preferably 6-20, particularly preferably 6 to 12 mol ethylene oxide of technical fatty acids with 12-18 carbon atoms, such as coconut, palm, palm kernel or tallow fatty acid, are also suitable.

Hair lightening or bleaching agents which are extremely preferred as contemplated herein contain at least one sodium polyacrylate with a weight-average molecular weight Mw in the range from about 1,000,000 to about 20,000,000 Daltons, preferably from about 6,000,000 to about 15,000,000 Daltons, in a total amount of from about 0.1-1.5% by weight, preferably from about 0.5-1.3% by weight, particularly preferably from about 0.8-1.1% by weight, each based on the weight of the agent. The sodium polyacrylate is pre-gelled in a water-in-oil emulsion, said water-in-oil emulsion, based in each case on its weight, includes from about 40-60% by weight sodium polyacrylate, a total of from about 25-45% by weight oil (s), preferably mineral oil, in total from about 0.5-4.9% by weight of surfactant (s), preferably from about 0.5-4.9% by weight non-ionic surfactant (s), and from about 0.5-4.9% by weight water.

Hair whitening or bleaching agents as contemplated herein, which contain sodium polyacrylate, have a viscosity in the range of from about 2,000 to about 70,000 mPas, preferably from about 10,000 to about 60,000 mPas, particularly preferably from about 20,000 to about 50,000 mPas, extremely preferably from about 35,000 to about 45,000 mPas, in each case measured at about 20° C. with a Brookfield rotational viscometer at a rotation frequency of 4 min-1 with spindle 5.

The hair whitening or bleaching agents as contemplated herein are further exemplified in that no crosslinked copolymer composed of acrylic acid and non-ethoxylated esters of acrylic acid with linear C10-C30 monoalcohols as monomers is contained.

An example of crosslinked copolymers built up from acrylic acid and non-ethoxylated esters of acrylic acid with linear C10-C30 monoalcohols as monomers, which are NOT included as contemplated herein, is the crosslinked copolymer of acrylic acid and non-ethoxylated esters of acrylic acid with linear C10-C30 monoalcohols with the INCI designation Acrylates/C10-30 Alkyl Acrylates Crosspolymer.

The hair brightening or bleaching agents as contemplated herein contain, in each case based on their weight, at least one linear saturated alkanol with two or three hydroxy groups and 2 to 8 carbon atoms in the alkyl group in a total amount of from about 0-3% by weight, preferably from about 0.1-2.2% by weight. Especially preferred linear saturated alkanols with two or three hydroxy groups and 2 to 8 carbon atoms in the alkyl group are selected from 1,2-propanediol and glycerol and mixtures thereof. It is extremely preferred to contain from about 0-3 wt. %, preferably from about 0.1-2.2 wt. % of about 1.2-propanediol, each based on the weight of the agent. Further preferred is at least one linear saturated alkanol with two or three hydroxy groups and 2 to 8 carbon atoms in the alkyl group, including 1,2-propanediol, in a total amount of from about 0-3% by weight, preferably from about 0.1-2.2% by weight, each based on the weight of the agent.

The agents according to and used in the present disclosure do not contain saturated and unsaturated non-alkoxylated alkanols with a hydroxy group and 1 to 50 carbon atoms in the alk(en)yl group; in particular, the agents as contemplated herein do not contain ethanol, isopropanol, linear fatty alcohols, such as cetyl or stearyl alcohol, and branched alkanols, such as 2-octyldodecanol.

Furthermore, the agents as contemplated herein do not contain any saturated and unsaturated alkanecarboxylic acids with 1 to 50 carbon atoms, in particular oleic acid and stearic acid or their salts.

Agents preferred and preferably used as contemplated herein contain, based on their weight, polyethylene glycol(s) with an average molecular weight of from about 100-100000 g-Mol$^{-1}$ in a total amount of from about 0-0.2 wt. %, preferably from about 0-0.1 wt. %. As contemplated herein, polyethylene glycols are compounds of the formula $HO(CH_2CH_2O)_nH$, where the index n indicates the degree of polymerization and is a number from about 3-2300.

It was found that saturated and unsaturated non-alkoxylated alkanols with one hydroxy group and 1 to 50 carbon atoms in the alk(en)yl group; in particular ethanol and isopropanol, further linear saturated alkanols with two or three hydroxy groups and 2 to 8 carbon atoms in the alkyl group and polyethylene glycols with an average molecular weight of from about 100 to 100000 g-Mol$^{-1}$ have an unfavourable effect on the nature of the gel consistency, so that their total content, as shown above, should be limited and as low as possible.

Furthermore, it is preferred that agents as contemplated herein and preferably used contain fatty substances with a melting point of about 30° C. and above at 1013 mbar and a water solubility of about 0.005 wt. % and below in a total amount of from about 0-0.1 wt. %, preferably 0 wt. %, based on the weight of the agent. These fatty substances include waxes, hardened oils and fats and esters of fatty acids and fatty alcohols with a melting point of about 30° C. and above at 1013 mbar.

Hair brightening or bleaching agents preferred as contemplated herein contain, in each case based on their weight, at least one oil in a total amount of from about 0.1 to about 2% by weight, preferably from about 0.2-1.5% by weight, particularly preferably from about 0.5-1% by weight.

The at least one oil which is contained in the hair whitening or bleaching agent (M1) preferred as contemplated herein in a total amount of from about 0.1 to 2 wt. %, preferably from about 0.2-1.5 wt. %, particularly preferably from about 0.5-1 wt. %, of the hair whitening or bleaching agent (M1) % by weight, in each case based on the weight of the agent (M1), is preferably selected from natural and synthetic hydrocarbons, particularly preferably mineral oil, paraffin oils, $C_{18}$-$C_{30}$-isoparaffins, in particular isoeicosan, polyisobutenes and polydecenes, $C_8$-$C_{16}$ isoparaffins, and 1,3-di(2-ethylhexyl)cyclohexane; the benzoic acid esters of linear or branched $C_{8-22}$ alkanols; triglycerides of linear or branched, saturated or unsaturated, optionally hydroxylated $C_{8-30}$-fatty acids, especially natural oils; the dicarboxylic acid esters of linear or branched $C_2$-$C_{10}$ alkanols; the esters of linear or branched, saturated or unsaturated fatty alcohols having 2-30 carbon atoms with linear or branched, saturated or unsaturated fatty acids having 2-30 carbon atoms which may be hydroxylated; the addition products of 1 to 5 propylene oxide units to mono- or polyvalent $C_{8-22}$-alkanols; the $C_8$-$C_{22}$ fatty alcohol esters of mono- or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the esters of dimers of unsaturated $C_{12}$-$C_{22}$-fatty acids (dimer fatty acids) with monovalent linear, branched or cyclic $C_2$-$C_{18}$-alkanols or with polyvalent linear or branched $C_2$-$C_6$-alkanols; silicone oils and mixtures of the aforementioned substances. Oils particularly preferred in this context as contemplated herein are selected from paraffin oils and the esters of linear or branched saturated or unsaturated fatty alcohols having 2-30 carbon atoms with linear or branched saturated or unsaturated fatty acids having 2-30 carbon atoms, which may be hydroxylated, and mixtures thereof; extremely preferably selected from mineral oil, paraffin oil, isopropyl palmitate and isopropyl myristate and mixtures thereof.

In a further preferred embodiment of the present disclosure, the hair whitening or bleaching agent as contemplated herein contains at least one ammonium salt of an inorganic acid or an organic acid with 1 to 7 carbon atoms and 1 to 3 carboxyl groups. With the aid of such ammonium salts, the pH value of the application mixture can be better buffered, which can improve the whitening performance of the agent as contemplated herein. Preferred ammonium salts of this type are selected from ammonium sulphate, ammonium hydrogen sulphate, ammonium chloride, ammonium carbonate, ammonium hydrogen carbonate, ammonium carbamate, ammonium nitrate, ammonium acetate, ammonium lactate, ammonium citrate, ammonium succinate, ammonium malate, ammonium maleate, ammonium tartrate, ammonium glycolate, ammonium gluconate and ammonium malonate and mixtures of the above salts. Particularly preferred ammonium salts of this type are selected from ammonium sulphate, ammonium hydrogen sulphate, ammonium chloride, ammonium carbonate, ammonium hydrogen carbonate, ammonium lactate, ammonium citrate, ammonium succinate and ammonium gluconate and mixtures of the above salts. Hair brightening or bleaching agents preferred as contemplated herein contain at least one ammonium salt of an inorganic acid or an organic acid with 1 to 7 carbon atoms and 1 to 3 carboxyl groups in a total amount of from about 0.01 to 5% by weight, preferably from about 0.1 to 4.5% by weight, particularly preferably from about 0.5 to 4% by weight, extremely preferably from about 1 to about 3% by weight, in each case based on the weight of the hair brightening or bleaching agent.

In another preferred embodiment of the present disclosure, the hair brightening, or bleaching agent of the present disclosure contains at least one direct dye.

In oxidative hair lightening or bleaching products, direct dyes are often used to nuance unwanted reddish tones, which can be produced by the melanin degradation products, or to nuance certain blonde tones.

In order to obtain a balanced and subtle nuance, it may also be provided within the scope of the present disclosure that the cosmetic hair lightening or bleaching preparations additionally contain at least one direct dye.

Direct dyes are dyes that are applied directly to the hair and do not require an oxidative process to develop the colour. Direct dyes are typically nitrophenylenediamines, nitroaminophenols, azo dyes, anthraquinones or indophenols.

Direct dyes can be divided into anionic, cationic and non-ionic direct dyes.

Preferred anionic direct dyes are the compounds known under the names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52 and Tetrabromophenol blue.

Preferred cationic substantive dyes are cationic triphenylmethane dyes, such as Basic Blue 7, Basic Blue 26, Basic Violet 2 and Basic Violet 14, and aromatic systems which are substituted with a quaternary nitrogen group, such as Basic Yellow 57, Basic Red 76, Basic Blue 99, Basic Brown 16 and Basic Brown 17 and HC Blue 16, as well as Basic Yellow 87, Basic Orange 31 and Basic Red 51.

Preferred non-ionic direct dyes are HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-Diamino-2-nitrobenzene, 2-Amino-4-nitrophenol, 1,4-(2-hydroxyethyl)amino-2-nitrobenzene, 3-Nitro-4-(2-hydroxyethyl)aminophenol, 2-(2-Hydroxyethyl)amino-4,6-dinitrophenol, 4-[(2-Hydroxyethyl)amino]-3-nitro-1-methylbenzene, 1-Amino-4-(2-hydroxyethyl)amino-5-chloro-2-nitrobenzene, 4-Amino-3-nitrophenol, 1-(2'-Ureidoethyl)amino-4-nitrobenzene, 2-[(4-Amino-2-nitrophenyl)amino]benzoic acid, 6-Nitro-1,2,3,4-tetrahydroquinoxaline, 2-Hydroxy-1,4-naphthoquinone, picramic acid and its salts, 2-Amino-6-chloro-4-nitrophenol, 4-Ethylamino-3-nitrobenzoic acid and 2-Chloro-6-ethylamino-4-nitrophenol.

Furthermore, naturally occurring dyes, such as those contained in henna red, henna neutral, henna black, chamomile flowers, sandalwood, black tea, walnut, rotten bark, sage, blue wood, madder root, catechu and alkanna root can also be used as direct dyes.

Preferably, the cosmetic composition contains at least one direct dye in a total amount of from about 0.001 to about 10% by weight, preferably from about 0.01 to about 8% by weight, preferably from about 0.1 to about 5% by weight, in particular from about 0.5 to about 2% by weight, each based on the total weight of the cosmetic composition or of the composition (M1) used as contemplated herein.

In a further preferred embodiment of the present disclosure, the hair whitening or bleaching agent of the present disclosure contains at least one aminated silicone. Preferred aminated silicones are selected from compounds of structural formula (I),

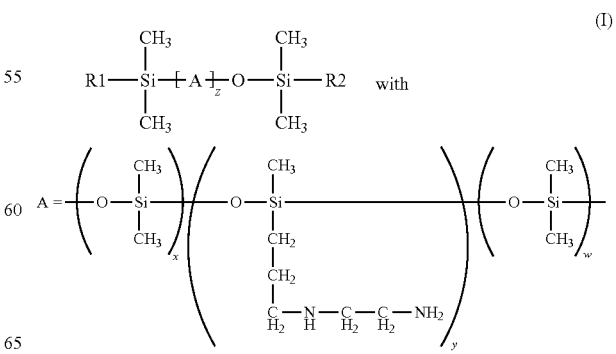

wherein
i. x and y stand independently for numbers from 1 to about 100,
ii. w stands for a number from 0 to about 100,
iii. z is a number from 1 to about 100, whereby, if z≥2, the respective values x, y and w in a structural element A can each be selected independently of preceding structural elements A
and
iv. R1 and R2 independently of one another represent a linear or branched, saturated, unsaturated or polyunsaturated $C_5$-$C_{20}$ alkyl group, a hydroxy group, a $C_1$-$C_{30}$ alkoxy group, a carboxy-$C_1$-$C_{30}$ alkyl group or a $C_1$-$C_6$ alkyl-(O—$CH_2$—$CH_2$)$_n$—O— group, wherein n is an integer from 1 to about 60.

The structural elements A of the compound of the formula (I) are each composed of one or more elements 3-[(2-aminoethyl)amino]propyl-methyl-siloxane and one or more elements dimethylsiloxane. The number of dimethylsiloxane elements is defined by the parameter x. The number of 3-[(2-aminoethyl)amino]propyl-methyl-siloxane elements is defined by the parameter y. As contemplated herein, the values of the parameters x and y stand independently of each other for numbers between 1 and about 100.

The number of structural elements A is defined by the parameter z. As contemplated herein, the value of the parameter z is between 1 and about 100. If z≥2, the parameters x and y can be selected in each structural element A independently of preceding structural elements A. It follows that for the case where z≥2, the individual structural elements A may differ from one another in their number of 3[(2-aminoethyl)amino]propyl-methyl-siloxane elements and/or in their number of dimethylsiloxane elements.

The siloxane backbone of the compound(s) of formula (I) is terminated at both ends by the radicals R1 and R2, where R1 and R2, independently of one another, may represent a linear or branched, saturated, unsaturated or polyunsaturated $C_5$-$C_{20}$ alkyl chain, a hydroxyl group, a $C_1$-$C_{30}$ alkoxy group or a $C_1$-$C_6$ alkyl-(O—$CH_2$—$CH_2$)$_n$—O— group.

If R1 and/or R2 stand for a branched, saturated, unsaturated or polyunsaturated $C_5$-$C_{20}$ alkyl radical, the siloxane skeleton is terminated with a fatty alkyl chain. Fatty alkyl chains in the sense of the present disclosure are all linear and/or branched, saturated and/or unsaturated and/or polyunsaturated carbon chains whose carbon chain is preferably a $C_6$-$C_{30}$ chain, particularly preferably a $C_8$-$C_{24}$ chain and particularly a $C_{14}$-$C_{20}$ chain. Examples of fatty alkyl chains as contemplated herein are hexyl, heptyl, octyl, nonyl, decyl, dodecyl, tetradecyl, pentadecyl, hexadecyl, heptadecyl, octadecyl, nonadecyl, eicosyl, docosyl, tetracosyl, hexacosyl, iso-stearyl, (9Z)-tetradeca-9-enyl, (9Z)-hexadeca-9-enyl, (6Z)-Octadeca-6-enyl, (9Z)-Octadeca-9-enyl, (9E)-Octadeca-9-enyl, (11E)-Octadeca-11-enyl, (9Z)-Eicosa-9-enyl, (11Z)-Eicosa-11-enyl, (11Z)-Docosa-11-enyl, (13Z)-Docosa-13-enyl, (15Z)-Tetracosa-15-enyl, (9Z,12Z)-Octadeca-9,12-dienyl, (9Z,12Z,15Z)-Octadeca-9,12,15-trienyl, (6Z,9Z,12Z)-Octadeca-6,9, 12-trienyl, (8E,10E, 12Z)-Octadeca-8, 10,12-trienyl, (9Z,11E,13Z)-Octadeca-9, 11,13-trienyl, (9Z,11E,13E)-Octadeca-9,11,13-trienyl, (9E, 11E, 13E)-Octadeca-9,11,13-trienyl, (5Z,8Z,11Z,14Z)-Eicosa-5,8,11,14-tetraenyl, (5Z,8Z,11Z,14Z,17Z)-Eicosa-5,8, 11,14 17-pentaenyl, (7Z,10Z,13Z, 16Z,19Z)-Docosa-7,10, 13,16,19-pentaenyl, and (4Z,7Z,10Z,13Z,16Z,19Z)-Docosa-4,7,10,13,16,19-hexaenyl. In a preferred embodiment of the present disclosure, the radicals $R^1$ and $R^2$ independently of one another represent linear alkyl chains, preferably $C_{14}$-$C_{20}$ alkyl, particularly preferably tetradecyl, pentadecyl, hexadecyl, heptadecyl, octadecyl, nonadecyl or eicosyl. Particularly preferred residues $R^1$ and/or $R^2$ are hexadecyl (cetyl) and/or octadecyl (stearyl). Cetearyl is a mixture of cetyl and stearyl; this mixture is also preferred.

In a preferred embodiment, the agent of the present disclosure contains a compound of formula (I) in which the substituents R1 and R2 independently of one another represent a linear or branched chain, saturated, unsaturated or polyunsaturated $C_5$-$C_{20}$-alkyl chain, preferably a linear $C_{14}$-$C_{20}$ alkyl chain, in particular preferably a representative from the group $H_3C$—$(CH_2)_{13}$—, $H_3C$—$(CH_2)_{15}$—, $H_3C$—$(CH_2)_{17}$—, and $H_3C$—$(CH_2)_{19}$—.

As contemplated herein, compounds of the formula (I) in which the radicals $R^1$ and $R^2$ independently of one another represent $H_3C$—$(CH_2)_{15}$— or $H_3C$—$(CH_2)_{17}$— are particularly preferred. In this case, the amodimethicone is a bis-tearyl amodimethicone.

In a further preferred embodiment, an agent as contemplated herein contains at least one compound of formula (I) in which $R^1$ is $H_3C$—$(CH_2)_{15}$— or $H_3C$—$(CH_2)_{17}$— and $R^2$ is $H_3C$—$(CH_2)_{15}$— or $H_3C$—$(CH_2)_{17}$—. Such compounds are known under the INCI designation Bis-Cetearyl Amodimethicone, which is commercially available for example under the trade name Silsoft AX from the company Momentive.

A particularly preferred hair brightening, or bleaching agent contains at least one compound of formula (Ia), (Ib) and/or (Ic),

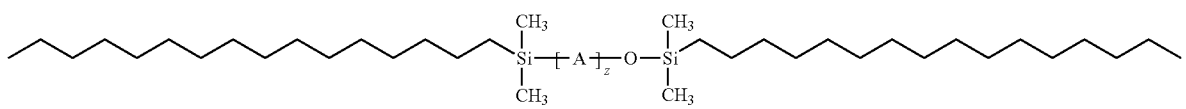

(Ia)

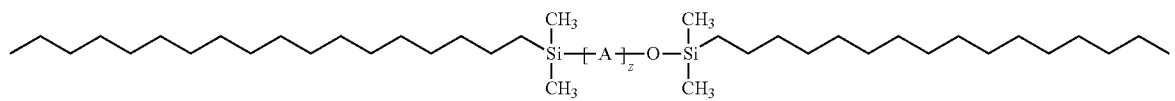

(Ib)

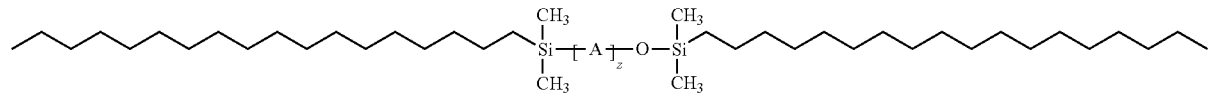

(Ic)

where the structural unit (A) in the formulae (Ia), (Ib), (Ic) each independently of one another is

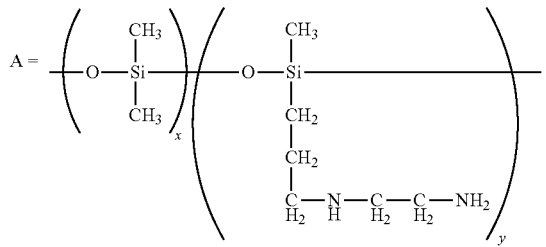

wherein
x and y independently of each other stand for values between 1 and 100,
z stands for values between 1 and 100, whereby, if z≥2, the respective values x and y in a structural element A can each be selected independently of preceding structural elements A.

A further aminated silicone preferred as contemplated herein is selected from at least one compound of structural formula (II),

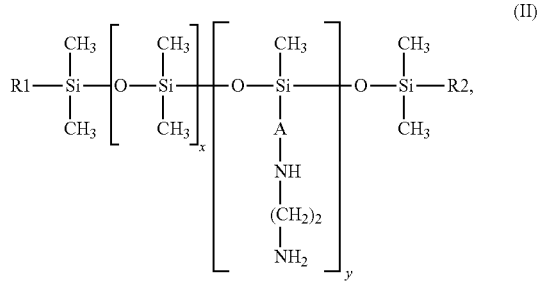

wherein
i. x and y independently of one another stand for numbers from 1 to about 5000, where x preferably stands for numbers from about 10 to about 1800 and particularly preferably from about 100 to about 1000, where y preferably stands for numbers from 1 to about 80,
ii. R1 and R2 independently represent a methyl group or a hydroxy group, and
iii. A represents a linear or branched alkylene group with 2 to 8, preferably 3-6 and particularly preferably 3 or 4 carbon atoms, preferably a linear propylene group —CH$_2$—CH$_2$—CH$_2$— or a branched isobutylene group —CH$_2$—CH(CH$_3$)—CH$_2$.

Another aminated silicone preferred by the present disclosure is selected from at least one linear copolymer comprising blocks of polydimethylsiloxane units and blocks of polyethylene glycol bis(2-methyl-2-propen-1-yl)ether monomers having the following structure (III)

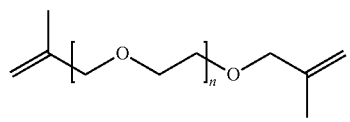

(III)

where n=14 and which is terminated with 3-{3-[bis(2-hydroxypropyl)amino]-2-hydroxypropoxy]propyl groups. A preferred linear copolymer of this type has the INCI designation Bis-Diisopropanolamino-PG-Propyl-Dimethicone/Bis-Isobutyl PEG-14 Copolymer. This linear copolymer is available in emulsified form under the trade name DC CE-8411 Smooth Plus Emulsion from Dow Corning.

Whitening or bleaching agents preferred as contemplated herein contain at least one aminated silicone selected from compounds of structural formula (I), compounds of structural formula (II), linear copolymers comprising blocks of polydimethylsiloxane units and blocks of polyethylene glycol bis(2-methyl-2-propen-1-yl)ether monomers of structure (III) below

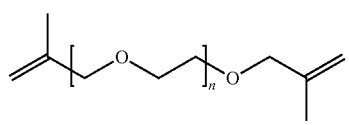

(III)

where n=14 and which are terminated with 3-{3-[bis(2-hydroxypropyl)amino]-2-hydroxypropoxy]propyl groups, and mixtures of these compounds.

Other whitening or bleaching agents preferred as contemplated herein contain at least one aminated silicone selected from compounds of structural formula (I), compounds of structural formula (II), linear copolymers containing blocks of polydimethylsiloxane units and blocks of polyethylene glycol bis(2-methyl-2-propen-1-yl)ether monomers of structure (III) below

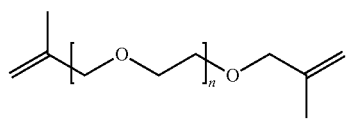

(III)

where n=14 and which are terminated with 3-{3-[bis(2-hydroxypropyl)amino]-2-hydroxypropoxy]propyl groups, and mixtures of these compounds, in a total amount of from about 0.01-5% by weight, preferably from about 0.1-3% by weight, particularly preferably from about 0.5 to 2% by weight, extremely preferably from about 1-1.5% by weight, in each case based on the weight of the whitening or bleaching agent.

Optional Blonde Booster

Optionally, an anhydrous persulphate and/or percarbonate-containing composition can be added to the mixture of the agent as contemplated herein or the agent preferred as contemplated herein and an aqueous hydrogen peroxide preparation, thereby further enhancing the whitening and bleaching performance of the agent. The anhydrous persulphate and/or percarbonate containing composition is often also called bleach booster or blonde booster.

The blond booster preferred by the present disclosure is in powder form.

As contemplated herein, the term "powder" or "powdery" means a solid, free-flowing dosage form including individual particles that are solid at about 20° C. and 1013 mbar, in which the particles have particle sizes ranging from about 0.1 μm to a maximum of about 1.6 mm. The determination of particle sizes can preferably be done by laser diffraction measurement according to ISO 13320-1 (2009). If necessary, the particle size of the blonde booster can be adjusted by physical treatment, such as sieving, pressing, granulating or pelletising, or by the addition of certain auxiliary substances, to meet the requirements of the blonde booster, for example to allow better miscibility of the individual powder constituents or miscibility of the blonde booster with the agent of the present disclosure and an aqueous hydrogen peroxide preparation.

Blond boosters preferably used in accordance with the present disclosure have a bulk density in the range of from about 500 to about 1000 g/l (grams/litre), preferably from about 550 to about 900 g/l, particularly preferably from about 600 to about 820 g/l. The determination of the bulk density is preferably carried out according to EN ISO 600 DIN 53468.

Unless otherwise stated, all temperature specifications refer to a pressure of 1013 mbar.

The blonde booster preferably used as contemplated herein contains as the first essential ingredient at least one oxidizing agent selected from sodium percarbonates and inorganic salts of a peroxosulfuric acid and mixtures thereof.

Sodium percarbonates are sodium carbonate-hydrogen peroxide complexes. Commercial sodium percarbonate has the average composition $2\ Na_2CO_3 \cdot 3\ H_2O_2$. Sodium percarbonate is present as a white, water-soluble powder that easily breaks down into sodium carbonate and "active" oxygen that has a bleaching and oxidizing effect.

Peroxosulphuric acids are peroxodisulphuric acid and peroxomonosulphuric acid (Caro's acid).

Preferably at least one inorganic salt of peroxosulphuric acid is selected from ammonium peroxodisulphate, alkali metal peroxodisulphates, ammonium peroxomonosulphate, alkali metal peroxomonosulphates and alkali metal hydrogen peroxomonosulphates. Ammonium peroxodisulfate, potassium peroxodisulfate, sodium peroxodisulfate and potassium hydrogen peroxomonosulfate are particularly preferred. Furthermore, during the work on the present disclosure, it has proved to be particularly preferred if the blonde booster preferably used as contemplated herein contains at least two different peroxodisulfates. Preferred peroxodisulfate salts are combinations of ammonium peroxodisulfate and potassium peroxodisulfate and/or sodium peroxodisulfate.

Blonde boosters preferably used as contemplated herein contain at least one oxidizing agent selected from sodium percarbonates and inorganic salts of a peroxosulfuric acid and mixtures thereof in a total amount of from about 5-100% by weight, preferably from about 10-98% by weight, particularly preferably from about 25-70% by weight, extremely preferably from about 30-50% by weight, in each case based on the weight of the blonde booster.

The water-free blonde boosters preferably used as contemplated herein have a water content of from 0 to about 8% by weight, preferably from about 0.1 to about 5% by weight, particularly preferably from about 0.5 to about 2.5% by weight, of water, in each case based on the weight of the blonde booster. With the above-mentioned water contents ranging from 0 to about 8% by weight, blonde boosters are, by definition, regarded as anhydrous for the purposes of the present application. These figures refer to the content of free water. Not considered is the content of molecularly bound water or water of crystallization, which individual powder components may have.

The water content can be determined by Karl Fischer titration according to ISO 4317 (Version 2011-12).

Blond boosters preferably used in accordance with the present disclosure preferably additionally contain at least one inorganic alkalizing agent which is solid at about 20° C. and 1013 mbar and which is preferably contained in a total amount of from about 1-60% by weight, preferably from about 5-55% by weight, particularly preferably from about 10-50% by weight, extremely preferably from about 15-45% by weight, in each case based on the weight of the blond booster. As contemplated herein, particularly preferred inorganic alkalizing agents which are solid at about 20° C. and 1013 mbar are selected from alkali metal silicates, alkaline earth metal silicates, alkaline earth metal hydroxide carbonates, alkaline earth metal carbonates, alkali metal hydroxides, alkaline earth metal hydroxides, (earth) alkali metal phosphates and (earth) alkali metal hydrogen phosphates and mixtures of these substances. As contemplated herein, particularly preferred inorganic alkalizing agents which are solid at about 20° C. and 1013 mbar are selected from sodium silicates with a molar SiO2/Na2O ratio of ≥2, preferably from about 2.5 to about 3.5, and from magnesium hydroxide carbonates and mixtures of these substances. As contemplated herein, preferred magnesium hydroxide carbonates are those with the formula $MgCO_3 \cdot Mg(OH)_2 \cdot 2\ H_2O$ and those with the formula $MgCO_3 \cdot Mg(OH)_2$. Magnesium hydroxide carbonate with the formula $MgCO_3 \cdot Mg(OH)_2$ is particularly preferred as contemplated herein.

Blond boosters which are used with particular preference as contemplated herein contain, in each case based on their total weight, from about 20-50% by weight, preferably from about 22-40% by weight, particularly preferably from about 23-30% by weight of sodium silicates with a molar $SiO_2/Na_2O$ ratio of ≥2, preferably from about 2.5 to about 3.5.

Further blond boosters preferably used as contemplated herein contain, based on their total weight, from about 20-50% by weight, preferably from about 30-45% by weight, particularly preferably from about 34-40% by weight of sodium silicates with a molar $SiO_2/Na_2O$ ratio of ≥2, preferably from about 2.5 to about 3.5, and from about 2 to about 20% by weight, preferably from about 5 to about 15% by weight, particularly preferably from about 10 to about 13% by weight of magnesium hydroxide carbonate with the formula $MgCO_3 \cdot Mg(OH)_2$ as an inorganic alkalizing agent which is solid at about 20° C. and 1013 mbar.

Another object of the present disclosure is a packaging unit (kit-of-parts) which—packed separately—comprises the following:

a) at least one container (C1) containing an agent for oxidative hair lightening or bleaching which contains, in each case based on its weight:
  from about 70-95% by weight water,
  at least one alkalizing agent,
  at least one surfactant selected from anionic, zwitterionic and amphoteric surfactants and mixtures thereof in a total amount of from about 0.1-2% by weight,
  Sodium polyacrylate in a total amount of from about 0.1-1.5% by weight, preferably from about 0.5-1.3% by weight, particularly preferably from about 0.8-1.1% by weight, preferably with a mass-average molar mass Mw in the range from about 1,000,000 to about 20,000,000 Daltons, preferably from about 6,000,000 to about 15,000,000 Daltons,
  at least one linear saturated alkanol with two or three hydroxy groups and 2 to 8 carbon atoms in the alkyl group in a total amount of from about 0-3% by weight,
  where
    no crosslinked copolymer composed of acrylic acid and non-ethoxylated esters of acrylic acid with linear C10-C30 monoalcohols as monomers, no saturated and unsaturated non-alkoxylated alkanols having a hydroxy group and 1 to 50 carbon atoms in the alk(en)yl group, no saturated and unsaturated alkanecarboxylic acids with 1 to 50 carbon atoms and no oxidizing agents are contained, wherein the agent has a pH value in the range from about 10.0 to about 11.0, preferably in the range from about 10.1 to about 10.8, each measured at about 20° C., and b) at least one container (C2) containing an oxidizing agent preparation (M2), which contains from about 40-96% by weight, preferably from about 70-93% by weight, particularly preferably from about 80-90% by weight, water, furthermore hydrogen peroxide in a total amount of from about 0.5 to about 23% by weight, more preferably from about 2.5 to about 21% by weight, particularly preferably from about 4 to about 20% by weight, very particularly preferably from about 5 to about 18% by weight and extremely preferably from about 6-12% by weight, and has a pH value in the range from about 2.0 to about 6.5, preferably from about 2.5-5.5, particularly preferably from about 2.8 to about 5.0, in each case measured at about 20° C., the percentages by weight being based in each case on the weight of the oxidizing agent preparation (M2).

Another object of the present disclosure is a packaging unit (kit-of-parts) which—packed separately—comprises the following:

a) at least one container (C1) containing an agent for oxidative hair lightening or bleaching which contains, in each case based on its weight:

from about 70-95% by weight water, at least one alkalizing agent, at least one surfactant selected from anionic, zwitterionic and amphoteric surfactants and mixtures thereof in a total amount of from about 0.1-2% by weight, Sodium polyacrylate in a total amount of from about 0.1-1.5% by weight, preferably from about 0.5-1.3% by weight, particularly preferably from about 0.8-1.1% by weight, preferably with a mass-average molar mass Mw in the range from about 1,000,000 to about 20,000,000 Daltons, preferably from about 6,000,000 to about 15,000,000 Daltons, at least one linear saturated alkanol with two or three hydroxy groups and 2 to 8 carbon atoms in the alkyl group in a total amount of from about 0-3% by weight, where no crosslinked copolymer composed of acrylic acid and non-ethoxylated esters of acrylic acid with linear C10-C30 monoalcohols as monomers, no saturated and unsaturated non-alkoxylated alkanols having a hydroxy group and 1 to 50 carbon atoms in the alk(en)yl group, no saturated and unsaturated alkanecarboxylic acids with 1 to 50 carbon atoms and no oxidizing agents are contained, wherein the agent has a pH value in the range from about 10.0 to about 11.0, preferably in the range from about 10.1 to about 10.8, each measured at about 20° C., and b) at least one container (C2) containing an oxidizing agent preparation (M2), which contains from about 40-96% by weight, preferably from about 70-93% by weight, particularly preferably from about 80-90% by weight, water, furthermore hydrogen peroxide in a total amount of from about 0.5 to about 23% by weight, more preferably from about 2.5 to about 21% by weight, particularly preferably from about 4 to about 20% by weight, very particularly preferably from about 5 to about 18% by weight and extremely preferably from about 6-12% by weight, and has a pH value in the range from about 2.0 to about 6.5, preferably from about 2.5-5.5, particularly preferably from about 2.8 to about 5.0, in each case measured at about 20° C., the percentages by weight being based in each case on the weight of the oxidant preparation (M2), and c) at least one container (C3) containing a, preferably powdery, blonde booster composition (M3) comprising at least one oxidizing agent selected from sodium percarbonates and inorganic salts of a peroxosulfuric acid and mixtures thereof, in a total amount of 5-100 wt. %, preferably from about 10-98%, particularly preferably from about 25-70%, extremely preferably from about 30-50%, by weight, in each case based on the weight of the blond booster, and from 0 to about 8%, preferably from about 0.1 to about 5%, particularly preferably from about 0.5 to about 2.5%, by weight of water, in each case based on the weight of the blond booster.

As contemplated herein, preferred three-part blonding kits including the above-mentioned components (M1), (M2) and (M3) are composed with respect to the weight ratio (M1):(M2):(M3) of the three components to each other in such a way that the weight ratio (M1):(M2) is in the range of from about 1:0.8 to about 1:2.5, preferably from about 1:1 to about 1:2, and (M3) is present in an amount of from about 5-25 wt. %, preferably from about 7-20 wt. %, particularly preferably from about 7.5-17 wt. %, based on the weight of the total mixture of (M1), (M2) and (M3).

What has been said above and below for the preferred embodiments of the present disclosure applies mutatis mutandis to the present disclosure regarding Blonding Kits.

A further subject of the present disclosure is a process for oxidative hair lightening or bleaching which comprises the following process steps:

i) Provision of a cosmetic composition (M1) for oxidative hair lightening or bleaching, comprising from about 70-95% by weight water, at least one alkalizing agent, at least one surfactant selected from anionic, zwitterionic and amphoteric surfactants and mixtures thereof in a total amount of from about 0.1-2% by weight, Sodium polyacrylate in a total amount of from about 0.1-1.5% by weight, preferably from about 0.5-1.3% by weight, particularly preferably from about 0.8-1.1% by weight, preferably with a mass-average molar mass Mw in the range from about 1,000,000 to about 20,000,000 Daltons, preferably from about 6,000,000 to about 15,000,000 Daltons, at least one linear saturated alkanol with two or three hydroxy groups and 2 to 8 carbon atoms in the alkyl group in a total amount of from about 0-3% by weight, where no crosslinked copolymer composed of acrylic acid and non-ethoxylated esters of acrylic acid with linear C10-C30 monoalcohols as monomers, no saturated and unsaturated non-alkoxylated alkanols having a hydroxy group and 1 to 50 carbon atoms in the alk(en)yl group, no saturated and unsaturated alkanecarboxylic acids with 1 to 50 carbon atoms and no oxidizing agents are contained, wherein the agent has a pH value in the range from about 10.0 to about 11.0, preferably in the range from about 10.1 to about 10.8, each measured at about 20° C., and ii) Provision of an oxidizing agent preparation (M2), containing from about 40-96 wt. %, preferably from about 70-93 wt. %, particularly preferably from about 80-90 wt. %, water, furthermore hydrogen peroxide in a total amount of from about 0.5 to about 23 wt. %, more preferably from about 2.5 to about 21 wt. %, particularly preferably from about 4 to about 20 wt. %, most preferably from about 5 to about 18 wt. %, and extremely preferably from about 6 to about 12% by weight, and having a pH value in the range from about 2.0 to about 6.5, preferably from about 2.5-5.5, particularly preferably from about 2.8 to about 5.0, in each case measured at about 20° C., the percentages by weight being based in each case on the weight of the oxidizing agent preparation (M2), optionally containing at least one cationic surfactant, iii) Mixing of the cosmetic agent (M1) with the oxidizing agent preparation (M2), preferably in a weight ratio (M1):(M2) in the range of from about 1:0.8 to about 1:2.5, preferably from about 1:1 to about 1:2, immediately afterwards iv) Apply the mixture obtained in step iii) to the hair and leaving this mixture on the hair for a time of from about 1 to about 60 minutes, preferably of from about 20 to about 45 minutes, at room temperature and/or at from about 30-60° C., preferably at from about 32-50° C., v) rinsing the hair with water and/or a cleansing composition, and vi) if necessary, apply an after-treatment agent to the hair and rinse if necessary, followed by drying.

A further subject of the present disclosure is a process for oxidative hair lightening or bleaching which comprises the following process steps:

i) Provision of a cosmetic composition (M1) for oxidative hair lightening or bleaching, comprising from about 70-95% by weight water, at least one alkalizing agent, at least one surfactant selected from anionic, zwitterionic and amphoteric surfactants and mixtures thereof in a total amount of from about 0.1-2% by weight, Sodium polyacrylate in a total amount of from about 0.1-1.5% by weight, preferably from about 0.5-1.3% by weight, particularly preferably from about 0.8-1.1% by weight, preferably with a mass-average molar mass Mw in the range from about 1,000,000 to about 20,000,000 Daltons, preferably from about 6,000,000 to about 15,000,000 Daltons, at least one linear saturated alkanol with two or three hydroxy groups and 2 to 8 carbon atoms in the alkyl group in a total amount of from about 0-3% by weight, where no crosslinked copolymer composed of acrylic acid and non-ethoxylated esters of acrylic acid with linear C10-C30 monoalcohols as monomers, no saturated and unsaturated non-alkoxylated alkanols having a hydroxy group and 1 to 50 carbon atoms in the alk(en)yl group, no saturated and unsaturated alkanecarboxylic acids with 1 to 50 carbon atoms and no oxidizing agents are contained, wherein the agent has a pH value in the range from about 10.0 to about 11.0, preferably in the range from about 10.1 to about 10.8, each measured at about 20° C., and ii) Provision of an oxidizing agent preparation (M2), containing from about 40-96 wt. %, preferably from about 70-93 wt. %, particularly preferably from about 80-90 wt. %, water, furthermore hydrogen peroxide in a total amount of from about 0.5 to about 23 wt. %, more preferably from about 2.5 to about 21 wt. %, particularly preferably from about 4 to about 20 wt. %, most preferably from about 5 to about 18 wt. %, and extremely preferably from about 6 to about 12% by weight, and having a pH value in the range from about 2.0 to about 6.5, preferably from about 2.5-5.5, particularly preferably from about 2.8 to about 5.0, in each case measured at about 20° C., the percentages by weight being based in each case on the weight of the oxidizing agent preparation (M2), optionally containing at least one cationic surfactant, iii) Providing a, preferably powdery, blonde booster composition (M3) containing at least one oxidizing agent selected from sodium percarbonates and inorganic salts of a peroxosulfuric acid and mixtures thereof in a total amount of from about 5-100% by weight, preferably from about 10-98% by weight, particularly preferably from about 25-70% by weight, extremely preferably from about 30-50% by weight, in each case based on the weight of the blond booster, and from 0 to about 8% by weight, preferably from about 0.1 to about 5% by weight, particularly preferably from about 0.5 to about 2.5% by weight, of water, in each case based on the weight of the blond booster, iv) Mixing of the cosmetic agent (M1) with the oxidizing agent preparation (M2) and with the blonde booster composition (M3), preferably in such a weight ratio (M1):(M2):(M3) that the weight ratio (M1):(M2) is in the range of from about 1:0.8 to about 1:2.5, preferably from about 1:1 to about 1:2, and (M3) is present in an amount of from about 5-25 wt. %, preferably from about 7-20 wt. %, particularly preferably from about 7.5-17 wt. %, based on the weight of the total mixture of (M1), (M2) and (M3), and immediately thereafter, v) Applying the mixture obtained in step iv) to the hair and leaving this mixture on the hair for a time of from about 1 to about 60 minutes, preferably of from about 20 to about 45 minutes, at room temperature and/or at from about 30-60° C., preferably at from about 32-50° C., vi) rinsing the hair with water and/or a cleansing composition, and vii) if necessary, apply an after-treatment agent to the hair and rinse if necessary, followed by drying.

Processes preferred as contemplated herein for oxidative hair lightening or bleaching using the aforementioned components (M1), (M2) and (M3) are designed with respect to the weight ratio (M1):(M2):(M3) of the three components to one another in such a way that the weight ratio (M1):(M2) is in the range from about 1:0.8 to about 1:2.5, preferably from about 1:1 to about 1:2, and (M3) is present in an amount of from about 5-25 wt. % of the total weight of the three components, preferably from about 7-20 wt. %, particularly preferably from about 7.5-17 wt. %, based on the weight of the total mixture of (M1), (M2) and (M3).

The foregoing and subsequent provisions for the preferred embodiments of the present disclosure for Products (M1) (M2) and (M3) apply mutatis mutandis to the Oxidative Hair Lightening or Bleaching Processes as contemplated and described herein.

For oxidative hair whitening processes, the agent (M1) of the present disclosure, which contains one or more alkalizing agents and optionally one or more direct dyes, is usually mixed with an aqueous oxidizing agent-containing composition (M2) to form the ready-to-use hair whitening or bleaching agent immediately before application to the hair and then applied to the hair. In most cases, the agent (M1) as contemplated herein and the oxidant-containing composition (M2) are matched to one another in such a way that at a mixing ratio of from about 1 to about 1, based on parts by weight, an initial concentration of hydrogen peroxide of from about 0.5-12% by weight, preferably from about 2-10% by weight, particularly preferably from about 3-6% by weight of hydrogen peroxide (calculated as 100% H2O2), in each case based on the weight of the application mixture, is present in the finished application mixture. However, it is just as well possible to match the agent of the present disclosure (M1) and the oxidizing agent-containing composition (M2) in such a way that the concentrations required in the ready-to-use brightening or bleaching agent (application mixture) are obtained by mixing ratios other than 1:1, for example by a weight-related mixing ratio of from about 1:2 or about 1:3 or even about 2:3.

As contemplated herein, preferred weight-related mixing ratios (M1):(M2) are in the range from about 1:0.8 to about 1:2.5, particularly preferred in the range from about 1:1 to about 1:2.

As contemplated herein, the term "room temperature" refers to the temperature in the room in which a person usually uses a hair whitening or bleaching product, i.e. usually a bathroom or hairdressing salon, where the temperature is in the range from about 10-29° C.

Leaving the hair lightening application mixture in process step iv) in the hair lightening or bleaching processes as contemplated herein can also take place at least at about 30° C., preferably at from about 30-60° C., particularly preferably at from about 32-50° C., if the hair is heated, for example, with a heating hood or radiant heater.

The oxidizing agent preparation (M2) used in whitening or bleaching kits as contemplated herein and preferred in the present disclosure as well as in whitening or bleaching processes as contemplated herein and preferred in the present disclosure contains, in each case based on its weight, from about 40-96% by weight, preferably from about 70-93% by weight, particularly preferably from about 80-90% by weight, of water.

The oxidizing agent preparation (M2) used in whitening or bleaching kits as contemplated herein and preferred as contemplated herein as well as in hair whitening or bleaching processes as contemplated herein and preferred as contemplated herein further contains, in each case based on its weight, from about 0.5-23% by weight, more preferably from about 2.5-21% by weight, particularly preferably from about 4-20% by weight, very particularly preferably from about 5-18% by weight and extremely preferably from about 6-12% by weight, of hydrogen peroxide.

To stabilize the hydrogen peroxide, the oxidant preparation (M2) has a pH value in the range of from about 2.0 to about 6.5, preferably from about 2.5-5.5, particularly preferably from about 2.8 to about 5.0, each measured at about 20° C.

The viscosity of agents (M1) preferred as contemplated herein is in the range from about 2,000 to about 70,000 mPas, preferably from about 10,000 to about 60,000 mPas, particularly preferably from about 20,000 to about 50,000 mPas, extremely preferably from about 35,000 to about 45,000 mPas, in each case measured at about 20° C. with a Brookfield rotational viscometer at a rotation frequency of 4 min-1 with spindle 5, which is excellently suited for the handling of this agent itself (production, dosing to produce the mixture with the oxidant preparation).

Cationic Surfactant in the Oxidant Preparation (M2)

The oxidant preparation (M2) usually has a low viscosity in the range of from about 10-6000 mPas, preferably from about 200-5000 mPas, especially preferably from about 1000-4500 mPas, each measured at about 20° C. For application to the hair, however, the application mixture should have a significantly higher viscosity so that it remains on the hair during the entire application time (in the range of from about 5-60 minutes, preferably from about 30-45 minutes) and does not drip down. A distinction is made between whether the application mixture is prepared by shaking both compositions (M1) and (M2) in an application bottle, from which the application mixture is applied to the hair immediately after mixing with the aid of an application spout as a bottle top (bottle application), or whether the application mixture is prepared by mixing both compositions (M1) and (M2) in a bowl, from which the application mixture is applied to the hair with a brush immediately after mixing (brush application). The bottle application is particularly suitable for whitening or bleaching agents which are sold in retail outlets with a recommendation for use by the consumer himself. The brush application is particularly suitable for whitening or bleaching products that are produced in the hairdressing salon by the hairdresser and applied to the consumer's hair.

Surprisingly, it was found that an application mixture with a viscosity particularly suitable for brush application is obtained by mixing the agent (M1) according to the preferred present disclosure with an oxidizing agent preparation (M2) containing at least one cationic surfactant. During mixing, the interaction between the at least one sodium polyacrylate and the at least one cationic surfactant leads to the desired increase in viscosity. The resulting paste-like consistency of the application mixture leads to optimal application properties, especially for brush application. The application mixtures obtained in this way, particularly with weight-related mixing ratios (M1):(M2) in the range from about 1:0.8 to about 1:2.5, particularly preferably in the range from about 1:1 to about 1:2, preferably have a viscosity in the range from about 5,000-70,000 mPas, preferably from about 12,000-50,000 mPas, particularly preferably from about 15,000-23,000 mPas, in each case measured at about 20° C., with a Brookfield viscometer, at a rotation frequency of 4 min-1 with spindle No. 5.

In a further preferred embodiment of the present disclosure, the oxidant preparation (M2) used as contemplated herein contains at least one cationic surfactant, preferably in a total amount of from about 0.05-3% by weight, particularly preferably of from about 0.1-1.5% by weight, extremely preferably of from about 0.3-0.9% by weight, in each case based on the weight of the oxidant preparation (M2).

Cationic surfactants are surfactants, i.e. surface-active compounds, each with one or more positive charges. Cationic surfactants contain only positive charges. Usually these surfactants are composed of a hydrophobic part and a hydrophilic head group, the hydrophobic part usually including a hydrocarbon backbone (e.g. including one or two linear or branched alkyl chains) and the positive charge(s) being located in the hydrophilic head group. Cationic surfactants adsorb at interfaces and aggregate in aqueous solution above the critical micelle formation concentration to form positively charged micelles.

As contemplated herein, cationic surfactants of the type of quaternary ammonium compounds, esterquats and alkylamidoamines are preferred. Preferred quaternary ammonium compounds are ammonium halides, such as alkyltrimethylammonium chlorides, dialkyldimethylammonium chlorides, trialkylmethylammonium chlorides, as well as the imidazolium compounds known under the INCI designations Quaternium-27 and Quaternium-83. Other preferred quaternary ammonium compounds are tetraalkylammonium salts, such as in particular the quaternium-52 known under the INCI designation, a poly(oxy-1,2-ethanediyl), ((octadecylnitrilio)tri-2,1-ethanediyl)tris(hydroxy)phosphate (1:1) salt, which has the general structural formula (III), wherein x+y+z=10

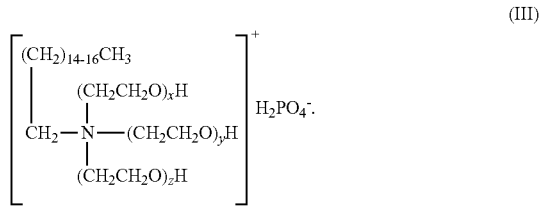

The long alkyl chains of the surfactants mentioned above preferably have 10 to 22, particularly preferably 12 to 18 carbon atoms. Behenyl trimethylammonium chloride, stearyl trimethylammonium chloride and cetyl trimethylammonium chloride are particularly preferred, with stearyl trimethylammonium chloride being extremely preferred. Further cationic surfactants suitable as contemplated herein are quaternized protein hydrolysates. Alkylamidoamines are usually produced by amidation of natural or synthetic fatty acids and fatty acid cuts with dialkylaminoamines Tegoamid® S 18 (stearamidopropyldimethylamine) is a suitable compound from this group of substances. Esterquats are substances which contain both at least one ester function and at least one quaternary ammonium group as a structural element. Preferred esterquats are quaternized ester salts of fatty acids with triethanolamine, quaternized ester salts of fatty acids with diethanolalkylamines and quaternized ester salts of fatty acids with 1.2-dihydroxypropyl dialkylamines. Such products are sold under the Stepantex, Dehyquart and Armocare trademarks.

In terms of optimum application properties and optimum whitening results, C10-C22 alkyl trimethyl ammonium chlorides have proven to be particularly suitable. Particularly preferred oxidizing agent preparations (M2) used in accordance with the present disclosure include at least one cationic surfactant in a total amount of from about 0.05-3% by weight, particularly preferably from about 0.1-1.5% by weight, extremely preferably from about 0.3 to about 0.9% by weight, based in each case on the weight of the oxidizing agent preparation (M2). Preferably at least one surfactant is selected from C10-C22-alkyltrimethylammonium chlorides, in particular selected from behenyltrimethylammonium chloride, stearyltrimethylammonium chloride and cetyltrimethylammonium chloride, and mixtures of these surfactants. Extremely preferred oxidizing agent preparations (M2) used as contemplated herein contain stearyltrimethylammonium chloride in a total amount of from about 0.05-3% by weight, particularly preferably from about 0.1-1.5% by weight, extremely preferably from about 0.3-0.9% by weight, each based on the weight of the oxidizing agent preparation (M2).

A further packaging unit (kit-of-parts) preferred as contemplated herein is exemplified in that the oxidizing agent preparation (M2) contains at least one cationic surfactant, preferably in a total amount of from about 0.05-3 wt. %, particularly preferably from about 0.1-1.5 wt. %, extremely preferably from about 0.3-0.9% by weight, in each case based on the weight of the oxidant preparation (M2), but contains no polymer with a degree of polymerization of at least about 200 and contains no polymer with a molecular weight of about 10,000 Daltons or higher.

It was found that the thickening by the interaction between the copolymer in the agent of the present disclosure and the cationic surfactant in the oxidizer preparation (M2) is sufficient and cannot be further increased or even impaired in its application properties by the presence of a polymer with a degree of polymerization of at least 200 or a polymer with a molecular weight of 10,000 Daltons or higher.

A further packaging unit (kit-of-parts) preferred as contemplated herein is exemplified in that the oxidizing agent preparation (M2) contains at least one cationic surfactant, preferably selected from stearyl trimethylammonium chloride, in a total amount of from about 0.05-3 wt. %, particularly preferably from about 0.1-1.5% by weight, extremely preferably from about 0.3-0.9% by weight, in each case based on the weight of the oxidant preparation (M2), but does not contain any polymer with a degree of polymerization of at least 200 and contains no polymer with a molecular weight of about 10,000 Daltons or higher.

A process for oxidative hair lightening or bleaching which is preferred as contemplated herein is exemplified in that the oxidizing agent preparation (M2) contains at least one cationic surfactant, preferably in a total amount of from about 0.05-3% by weight, particularly preferably of from about 0.1-1.5% by weight. %, extremely preferably from about 0.3-0.9% by weight, in each case based on the weight of the oxidant preparation (M2), but contains no polymer with a degree of polymerization of at least about 200 and contains no polymer with a molecular weight of about 10,000 Daltons or higher.

A further process, preferred as contemplated herein, for oxidative hair lightening or bleaching is exemplified in that the oxidizing agent preparation (M2) contains at least one cationic surfactant, preferably selected from stearyl trimethylammonium chloride, in a total amount of from about 0.05-3% by weight of %, particularly preferably from about 0.1-1.5% by weight, extremely preferably from about 0.3-0.9% by weight, in each case based on the weight of the oxidant preparation (M2), but does not contain any polymer with a degree of polymerization of at least about 200 and contains no polymer with a molecular weight of about 10,000 Daltons or higher.

Surprisingly, it was found that an application mixture with a viscosity particularly suitable for bottle application is obtained by mixing the agent (M1) according to the preferred present disclosure with an oxidizing agent preparation (M2) containing at least one copolymer selected from cross-linked acrylic acid/acrylic acid-C1-C6-alkyl ester copolymers and cross-linked methacrylic acid/acrylic acid-C1-C6-alkyl ester copolymers, preferably in a total amount of from about 0.1-7 wt.-%, particularly preferably from about 0.5-6% by weight, extremely preferably from about 1-4.5% by weight, in each case based on the weight of the oxidizing agent preparation (M2). Mixing the agent as contemplated herein or the preferred agent as contemplated herein with such an oxidizing agent preparation (M2) leads to the desired increase in viscosity. The resulting medium viscous consistency of the application mixture leads to optimal application properties, especially for bottle application. The application mixtures obtained in this way, especially with weight-related mixing ratios (M1):(M2) in the range from about 1:0.8 to about 1:2.5, particularly preferably in the range from about 1:1 to about 1:2, preferably have a viscosity in the range from about 2000-50,000 mPas, preferably from about 5000-40,000 mPas, particularly preferably from about 8,000-30,000 mPas, extremely preferably from about 11,000-24,000 mPas, in each case measured at about 20° C. with a Brookfield viscometer, at a rotation frequency of about 4 min-1 with spindle No. 5.

A further packaging unit (kit-of-parts) preferred as contemplated herein is therefore exemplified in that the oxidizing agent preparation (M2) contains at least one copolymer selected from crosslinked acrylic acid/acrylic acid-C1-C6-alkyl ester copolymers and crosslinked methacrylic acid/acrylic acid-C1-C6-alkyl ester copolymers, preferably in a total amount of from about 0.1-7 wt.-%, particularly preferably from about 0.5-6% by weight, extremely preferably from about 1-4.5% by weight, in each case based on the weight of the oxidizing agent preparation (M2), and preferably contains no cationic surfactant.

A further process for oxidative hair whitening or bleaching preferred as contemplated herein is therefore exemplified in that the oxidizing agent preparation (M2) contains at least one copolymer selected from crosslinked acrylic acid/acrylic acid-C1-C6-alkyl ester copolymers and crosslinked methacrylic acid/acrylic acid-C1-C6-alkyl ester copolymers, preferably in a total amount of from about 0.1-7 wt.-%, particularly preferably from about 0.5-6% by weight, extremely preferably from about 1-4.5% by weight, in each case based on the weight of the oxidizing agent preparation (M2), and preferably contains no cationic surfactant.

Preferred cross-linked copolymers of this type are selected from—respectively cross-linked—methacrylic acid/methyl acrylate, methacrylic acid/ethyl acrylate, methacrylic acid/propyl acrylate, methacrylic acid/butyl acrylate, methacrylic acid/pentyl acrylate, methacrylic acid/hexyl acrylate, acrylic acid/methyl acrylate, acrylic acid/ethyl acrylate, acrylic acid/propyl acrylate, acrylic acid/butyl acrylate, acrylic acid/pentyl acrylate and acrylic acid/hexyl acrylate copolymers and mixtures thereof.

A further packaging unit (kit-of-parts) preferred as contemplated herein is exemplified in that the oxidizing agent preparation (M2) contains at least one crosslinked copolymer selected from—respectively crosslinked—methacrylic acid/methyl acrylate, methacrylic acid/ethyl acrylate, methacrylic acid/propyl acrylate, methacrylic acid/butyl acrylate, methacrylic acid/pentyl acrylate, methacrylic acid/hexyl acrylate, acrylic acid/methyl acrylate, acrylic acid/ethyl acrylate, acrylic acid/propyl acrylate, acrylic acid/butyl acrylate, acrylic acid/pentyl acrylate and acrylic acid/hexyl acrylate copolymers and mixtures thereof, in a total amount of from about 0.1-7% by weight, particularly preferably from about 0.5-6% by weight, extremely preferably from about 1-4.5 wt.-%, based in each case on the weight of the oxidizing agent preparation (M2), and containing no cationic surfactant.

Another preferred method as contemplated herein for oxidative hair lightening or bleaching is exemplified in that the oxidizing agent preparation (M2) comprises at least one crosslinked copolymer, selected from—in each case crosslinked—methacrylic acid/methyl acrylate, methacrylic acid/ethyl acrylate, methacrylic acid/propyl acrylate, methacrylic acid/butyl acrylate, methacrylic acid/pentyl acrylate, methacrylic acid/hexyl acrylate, acrylic acid/methyl acrylate, acrylic acid/ethyl acrylate, acrylic acid/propyl acrylate, acrylic acid/butyl acrylate, acrylic acid/pentyl acrylate and acrylic acid/hexyl acrylate copolymers and mixtures thereof, in a total amount of from about 0.1-7% by weight, particularly preferably from about 0.5-6% by weight, extremely preferably from about 1-4.5% by weight, in each case based on the weight of the oxidizing agent preparation (M2), and contains no cationic surfactant.

The oxidizing agent preparations (M2) used as contemplated herein and preferably used as contemplated herein may also contain stabilizers, especially complexing agents, and pH buffer substances.

In a further preferred embodiment of the present disclosure, the oxidizing agent preparation (M2) used as contemplated herein contains at least one oil in a total amount of from about 0.2-50% by weight, preferably from about 2-40% by weight, particularly preferably from about 8-30% by weight, extremely preferably from about 10-25% by weight, in each case based on the weight of the oxidizing agent preparation (M2).

In a particularly preferred embodiment of the present disclosure, the oxidizing agent preparation (M2) used as contemplated herein contains no cationic surfactant and at least one oil in a total amount of from about 0.2-50% by weight, particularly preferably from about 2-40% by weight, extremely preferably from about 8-30% by weight, further extremely preferably from about 10-25% by weight, in each case based on the weight of the oxidizing agent preparation (M2).

The at least one oil present in the oxidizer preparation (M2) in a total amount of from about 0.2-50 wt. %, based on the weight of the preparation (M2), is preferably selected from natural and synthetic hydrocarbons, particularly preferably from mineral oil, paraffin oils, $C_{18}$-$C_{30}$-isoparaffins, in particular isoeicosane, polyisobutenes and polydecenes, $C_8$-$C_{16}$ isoparaffins, and 1,3-di(2-ethylhexyl)cyclohexane; the benzoic acid esters of linear or branched $C_{8-22}$ alkanols; triglycerides of linear or branched, saturated or unsaturated, optionally hydroxylated $C_{8-30}$-fatty acids, especially natural oils; the dicarboxylic acid esters of linear or branched $C_2$-$C_{30}$ alkanols; the esters of linear or branched, saturated or unsaturated fatty alcohols having 2-30 carbon atoms with linear or branched, saturated or unsaturated fatty acids having 2-30 carbon atoms which may be hydroxylated; the addition products of 1 to 5 propylene oxide units to mono- or polyvalent $C_{8-22}$-alkanols; the $C_8$-$C_{22}$ fatty alcohol esters of mono- or polyvalent $C_2$-$C_7$ hydroxycarboxylic acids; the symmetrical, asymmetrical or cyclic esters of carbonic acid with $C_{3-22}$ alkanols, $C_{3-22}$ alkanediols or $C_{3-22}$ alkanetriols; the esters of dimers of unsaturated $C_{12}$-$C_{22}$-fatty acids (dimer fatty acids) with monovalent linear, branched or cyclic $C_2$-$C_{18}$-alkanols or with polyvalent linear or branched $C_2$-$C_6$-alkanols; silicone oils and mixtures of the aforementioned substances. Oils particularly preferred in this connection as contemplated herein are selected from paraffin oils and the esters of linear or branched saturated or unsaturated fatty alcohols having 2-30 carbon atoms with linear or branched saturated or unsaturated fatty acids having 2-30 carbon atoms, which may be hydroxylated, and mixtures thereof; extremely preferably selected from paraffin oil, isopropyl palmitate and isopropyl myristate and mixtures thereof.

In a further preferred embodiment of the present disclosure, the oxidizing agent preparation (M2) used in accordance with the present disclosure contains at least one surfactant selected from anionic surfactants and non-ionic surfactants and mixtures thereof in a total amount of from about 0.05-2 wt. %, preferably from about 0.3-1.5 wt. %, of the oxidizing agent preparation (M2), and at least one linear, saturated 1-alkanol having 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of from about 1-5% by weight, preferably from about 1.5-4% by weight, all the quantitative data being based on the weight of the oxidizing agent preparation (M2), and the preparation (M2) containing no cationic surfactants, no oils, no polymer with a degree of polymerization of at least about 200 and no polymer with a molecular weight of about 10,000 Daltons or higher.

A further kit-of-parts preferred as contemplated herein and a further hair whitening process preferred as contemplated herein are each exemplified in that the oxidizing agent preparation (M2) contains at least one surfactant selected from anionic surfactants and non-ionic surfactants and mixtures thereof in a total amount of from about 0.05-2% by weight, preferably from about 0.3-1.5% by weight, of the total amount of the oxidizing agent preparation (M2), and at least one linear, saturated 1-alkanol having 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of from about 1-5% by weight, preferably from about 1.5-4% by weight, in each case based on the weight of the oxidant preparation (M2).

A further kit-of-parts preferred as contemplated herein and a further hair whitening process preferred as contemplated herein are each exemplified in that the oxidizing agent preparation (M2) contains at least one surfactant selected from anionic surfactants and non-ionic surfactants and mixtures thereof in a total amount of from about 0.05-2% by weight, preferably from about 0.3-1.5% by weight, of the total amount of the oxidizing agent preparation (M2), and at least one linear, saturated 1-alkanol having 14 to 22 carbon atoms, selected from 1-tetradecanol (myristyl alcohol), 1-hexadecanol (cetyl alcohol), 1-octadecanol (stearyl alcohol) and 1-eicosanol (arachyl alcohol) and mixtures thereof, in a total amount of from about 1-5% by weight %, preferably from about 1.5-4% by weight, in each case based on the weight of the oxidizing agent preparation (M2), but does not contain a polymer with a degree of polymerization of at least about 200 and does not contain a polymer with a molecular weight of about 10,000 Daltons or higher.

It was found that the thickening by the interaction between the copolymer in the agent of the present disclosure and the aforementioned surfactant/1-alkanol mixture in the oxidizer preparation (M2) is sufficient and cannot be further increased or even impaired in its application properties by the presence of a polymer with a degree of polymerization of at least about 200 or a polymer with a molecular weight of about 10,000 Daltons or higher.

A further kit-of-parts preferred as contemplated herein and a further hair whitening process preferred as contemplated herein are each exemplified in that the oxidizing agent preparation (M2) contains at least one surfactant selected from anionic surfactants and non-ionic surfactants and mixtures thereof in a total amount of from about 0.05-2% by weight, preferably from about 0.3-1.5% by weight, of the total amount of the oxidizing agent preparation (M2), and at least one linear, saturated 1-alkanol having 14 to 22 carbon atoms, selected from 1-tetradecanol, 1-hexadecanol, 1-octadecanol and 1-eicosanol and mixtures thereof, in a total amount of from about 1-5% by weight, preferably from about 1.5-4% by weight %, and at least one oil in a total amount of from about 0.2-50% by weight, preferably from about 2-40% by weight, particularly preferably from about 8-30% by weight, extremely preferably from about 10-25% by weight, in each case based on the weight of the oxidizing agent preparation (M2).

A further kit-of-parts and a further hair whitening method preferred as contemplated herein are each exemplified in that the oxidizing agent preparation (M2) contains at least one surfactant selected from anionic surfactants and non-ionic surfactants and mixtures thereof in a total amount of from about 0.05-2 wt. % of the total amount of the oxidizing agent preparation (M2), and preferably from about 0.3-1.5% by weight of at least one linear, saturated 1-alkanol having 14 to 22 carbon atoms, selected from 1-tetradecanol, 1-hexadecanol, 1-octadecanol and 1-eicosanol and mixtures thereof, in a total amount of from about 1-5% by weight %, preferably from about 1.5-4 wt. %, and at least one oil in a total amount of from about 0.2-50 wt. %, preferably from about 2-40 wt. %, particularly preferably from about 8-30 wt. %, extremely preferably from about 10-25 wt. %, in each case based on the weight of the oxidant preparation (M2), but not containing a polymer with a degree of polymerization of at least about 200 and not containing a polymer with a molecular weight of about 10,000 Daltons or higher As anionic surfactants, all anionic surfactants discussed above for the preparations of oxidizing agents (M2) used as contemplated herein are suitable for use with the preparations of oxidizing agents (M1).

Suitable as non-ionic surfactants for the oxidizing agent preparations (M2) used as contemplated herein are all non-ionic surface-active substances suitable for use on the human body which have at least one water-solubilizing, non-ionic group, in particular a polyethylene glycol ether group with at least 2 ethylene oxide units, a glycoside group, in particular a glucose or methylglucose group, a polyglycoside group with on average more than one glycoside unit, a polyglycerol group with at least two glycerol units, a sorbitan group, an amide group or several different ones of these groups, for example a sorbitan group and a polyethylene glycol ether group, and a lipophilic alkyl group with about 8 to 30 C atoms, preferably 10 to 24 C atoms. Non-ionic surfactants used with particular preference are selected from 7-80 moles of ethylene oxide per mole of ethoxylated castor oil, ethoxylated $C_8$-$C_{30}$-alkanols with 5-30 moles of ethylene oxide per mole, ethoxylated $C_8$-$C_{30}$-carboxylic acids with 5-30 moles of ethylene oxide per mole, with 4-50 moles of ethylene oxide per mole of ethoxylated sorbitan monoesters of linear saturated and unsaturated $C_{12}$-$C_{30}$-carboxylic acids, which can be hydroxylated, especially those of myristic acid, palmitic acid, stearic acid or of mixtures of these fatty acids, alkyl mono- and oligoglycosides with 8 to 22 carbon atoms in the alkyl radical and their ethoxylated analogues, and mixtures of the aforementioned substances.

The ethoxylated $C_8$-$C_{30}$-alkanols have the formula $R^1O(CH_2CH_2O)_nH$, where $R^1$ stands for a linear or branched alkyl and/or alkenyl radical with 8-30 carbon atoms and n, the average number of ethylene oxide units per molecule, for numbers from 4-100, preferably 6-30, particularly preferably 12 to 20 moles of ethylene oxide to 1 mole of alkanol, which is preferably selected from caprylic alcohol, 2-Ethylhexyl alcohol, capric alcohol, lauryl alcohol, isotridecyl alcohol, tridecyl alcohol, myristyl alcohol, cetyl alcohol, palmitoleyl alcohol, stearyl alcohol, Isostearyl alcohol, Oleyl alcohol, elaidyl alcohol, petroselinyl alcohol, arachyl alcohol, gadoleyl alcohol, behenyl alcohol, erucyl alcohol and brassidyl alcohol and from their technical mixtures. Adducts of 10-100 mol ethylene oxide to technical fatty alcohols with 12-18 carbon atoms, such as coconut, palm, palm kernel or tallow fatty alcohol, are also suitable. Trideceth-6, Isotrideceth-6, Undeceth-6, Myreth-6, Laureth-10, Laureth-12, Laureth-15, Laureth-20, Laureth-30, Myreth-10, Myreth-12, and Myreth-15 are particularly preferred. Myreth-20, Myreth-30, Ceteth-10, Ceteth-12, Ceteth-15, Ceteth-20, Ceteth-30, Steareth-10, Steareth-12, Steareth-15, Steareth-20, Steareth-30, Oleth-10, Oleth-12, Oleth-15, Oleth-20, Oleth-30, Ceteareth-10, Ceteareth-15, Ceteareth-12, Ceteareth-15, Ceteareth-20, Ceteareth-30 and Coceth-10, Coceth-12, Coceth-15, Coceth-20 and Coceth-30; Ceteth-10, Ceteth-12, Ceteth-15, Ceteth-20, Ceteth-30, Steareth-10, Steareth-12, Steareth-15, Steareth-20 and Steareth-30 and mixtures thereof are particularly preferred.

The ethoxylated $C_8$-$C_{30}$-carboxylic acids have the formula $R^1O(CH_2CH_2O)_nH$, where $R^1O$ stands for a linear or branched saturated or unsaturated acyl radical with 8-30 carbon atoms and n, the average number of ethylene oxide units per molecule, for numbers of 5-30, preferably 6-20, particularly preferably 6 to 12 moles of ethylene oxide with 1 mole of $C_8$-$C_{30}$-carboxylic acid, which is preferably selected from caprylic acid, 2-Ethylhexanoic acid, capric acid, lauric acid, isotridecanoic acid, myristic acid, cetylic acid, palmitoleic acid, stearic acid, isostearic acid, Oleic acid, elaidic acid, petroselinic acid, arachyic acid, gadoleic acid, behenic acid, erucic acid and brassidic acid and from their technical mixtures. Adducts of 5-30, preferably 6-20, particularly preferably 6 to 12 mol ethylene oxide of technical fatty acids with 12-18 carbon atoms, such as coconut, palm, palm kernel or tallow fatty acid, are also suitable.

With respect to the cosmetic agent (M1) in container C1 and the oxidizing agent preparation (M2) in container C2 of the present disclosure and the preferred present disclosure kits, the same applies mutatis mutandis to the present disclosure and preferred whitening or bleaching agents.

With respect to the cosmetic composition (M1) in container C1 of the oxidative hair lightening process as contemplated herein and preferred present disclosure, the same applies mutatis mutandis to the lightening or bleaching agents as contemplated herein and preferred present disclosure.

With respect to the oxidizing agent preparation (M2) in container C2 of the method for oxidative hair lightening as contemplated herein and preferred present disclosure, the same applies mutatis mutandis to the oxidizing agent preparations (M2) of the kits for oxidative hair lightening as contemplated herein and preferred present disclosure.

In summary, the subject matter of the present disclosure is summarized in the following points:

An agent for oxidative hair lightening or bleaching, containing, in each case based on the weight of the agent,
from about 70-95% by weight water,
at least one alkalizing agent,
at least one surfactant selected from anionic, zwitterionic and amphoteric surfactants and mixtures thereof in a total amount of from about 0.1-2% by weight,
Sodium polyacrylate in a total amount of from about 0.1-1.5% by weight, preferably from about 0.5-1.3% by weight, particularly preferably from about 0.8-1.1% by weight, preferably with a mass-average molar mass Mw in the range from about 1,000,000 to about 20,000,000 Daltons, preferably from about 6,000,000 to about 15,000,000 Daltons,
at least one linear saturated alkanol with two or three hydroxy groups and 2 to 8 carbon atoms in the alkyl group in a total amount of from about 0-3% by weight,
where
no crosslinked copolymer composed of acrylic acid and non-ethoxylated esters of acrylic acid with linear C10-C30 monoalcohols as monomers,
no saturated and unsaturated non-alkoxylated alkanols having a hydroxy group and 1 to 50 carbon atoms in the alk(en)yl group,
no saturated and unsaturated alkanecarboxylic acids with 1 to 50 carbon atoms and
no oxidizing agents
are contained,
exemplified in that the agent has a pH value in the range from about 10.0 to about 11.0, preferably in the range from about 10.1 to about 10.8, each measured at about 20° C.

The agent according to point 1, exemplified in that the alkalizing agent is selected from the group comprising ammonium hydroxide, basic amino acids, alkali metal hydroxides, alkanolamines, alkali metal silicates, alkali metal phosphates and alkali metal hydrogen phosphates and mixtures thereof.

The agent according to point 1 or 2, exemplified in that the at least one anionic or zwitterionic surfactant is selected from $C_8$-$C_{20}$ alkyl sulphates, $C_8$-$C_{20}$ alkyl ether sulphates and $C_8$-$C_{20}$-ether carboxylic acids, each with 8 to 20 C atoms in the alkyl group and 0 to 12 ethylene oxide groups in the molecule, where sodium laureth (2) sulphate is particularly preferred, further from cocoacylaminopropyl dimethylammonium glycinate and from mixtures of these surfactants, preferably at least one anionic or zwitterionic surfactant in a total amount of from about 0.3-1.5 wt. %, preferably from about 0.5-1.2% by weight, each based on the weight of the agent.

The agent according to one of the points 1-3, exemplified in that the sodium polyacrylate has a mass-average molar mass $M_w$ in the range from about 1,000,000 to about 20,000,000 Daltons, preferably from about 6,000,000 to about 15,000,000 Daltons.

The agent according to one of points 1-4, exemplified in that the sodium polyacrylate is contained as pregelled in a water-in-oil emulsion.

The agent according to point 5, exemplified in that said water-in-oil emulsion contains, in each case based on its weight, from about 40-60% by weight of sodium polyacrylate, a total of from about 25-45% by weight of oil(s), preferably mineral oil, a total of from about 0.5-4.9% by weight of surfactant(s), preferably from about 0.5-4.9% by weight of non-ionic surfactant(s), and from about 0.5-4.9% by weight of water.

The agent according to one of the points 1-6, exemplified in that at least one alkalizing agent, selected from ammonium hydroxide, basic amino acids, alkali metal hydroxides, alkanolamines, alkali metal silicates, alkali metal phosphates and alkali metal hydrogen phosphates and mixtures thereof, is added to the mixture in a total amount of from about 2-10% by weight, preferably from about 3-9% by weight, particularly preferably from about 4-8% by weight, extremely preferably from about 4.5-7% by weight, based on the weight of the hair brightening or bleaching agent as contemplated herein.

The agent according to one of the points 1-7, exemplified in that at least one ammonium salt of an organic acid with 1 to 7 carbon atoms and 1 to 3 carboxyl groups or an inorganic acid is contained.

The agent according to point 8, exemplified in that the ammonium salt is selected from ammonium sulphate, ammonium hydrogen sulphate, ammonium chloride, ammonium carbonate, ammonium hydrogen carbonate, ammonium carbamate, ammonium nitrate, ammonium acetate, ammonium lactate, ammonium citrate, ammonium succinate, ammonium malate, ammonium maleate, ammonium tartrate, ammonium glycolate, ammonium gluconate and ammonium malonate and mixtures of these salts, preferably selected from ammonium sulphate, ammonium hydrogen sulphate, ammonium chloride, ammonium carbonate, ammonium hydrogen carbonate, ammonium lactate, ammonium citrate, ammonium succinate and ammonium gluconate and mixtures of these salts.

The agent according to one of points 8 or 9, exemplified in that at least one ammonium salt of an organic acid with 1 to 7 carbon atoms and 1 to 3 carboxyl groups or an inorganic acid is contained in a total amount of from about 0.01 to about 5% by weight, preferably from about 0.1 to about 4.5% by weight, particularly preferably from about 0.5 to about 4% by weight, extremely preferably from about 1 to about 3% by weight, in each case based on the weight of the agent.

The agent according to one of points 1-10, exemplified by a viscosity in the range from about 2,000 to about 70,000 mPas, preferably from about 10,000 to about 60,000 mPas, particularly preferably from about 20,000 to about 50,000 mPas, extremely preferably from about 35,000 to about 45,000 mPas, in each case measured at about 20° C. with a Brookfield rotational viscometer at a rotational frequency of 4 min-1 with spindle 5.

The agent according to one of points 1-11, exemplified in that it further contains at least one aminated silicone, preferably selected from compounds of structural formula (I)

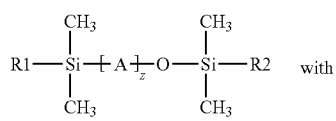

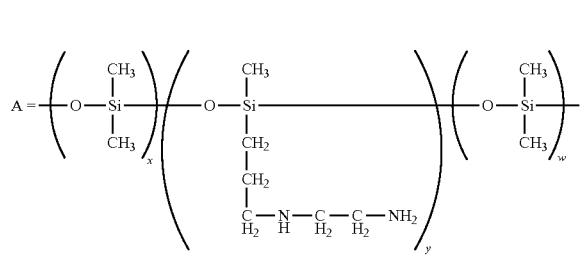

wherein
i. x and y stand independently for numbers from 1 to 100,
ii. w stands for a number from 0 to about 100,
iii. z is a number from 1 to about 100, whereby, if z≥2, the respective values x, y and w in a structural element A can each be selected independently of preceding structural elements A
and
iii. R1 and R2 independently of one another represent a linear or branched, saturated, unsaturated or polyunsaturated $C_5$-$C_{20}$ alkyl group, a hydroxy group, a $C_1$-$C_{30}$ alkoxy group, a carboxy-$C_1$-$C_{30}$ alkyl group or a $C_1$-$C_6$ alkyl-(O—$CH_2$—$CH_2$)$_n$—O— group, wherein n is an integer from 1 to about 60; and
compounds of structural formula (II),

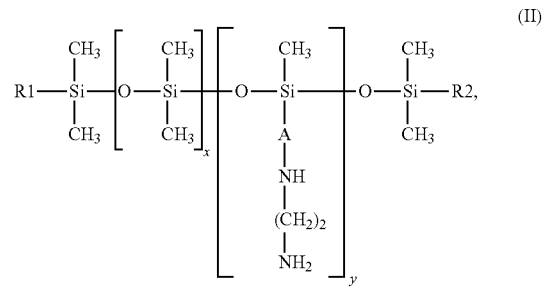

wherein
i. x and y independently of one another stand for numbers from 1 to about 5000, where x preferably stands for numbers from about 10 to about 1800 and particularly preferably from about 100 to about 1000, where y preferably stands for numbers from 1 to about 80,
ii. R1 and R2 independently represent a methyl group or a hydroxy group, and
iii. A represents a linear or branched alkylene group with 2 to 8, preferably 3-6 and particularly preferably 3 or 4 carbon atoms, preferably a linear propylene group —$CH_2$—$CH_2$—$CH_2$— or a branched isobutylene group —$CH_2$—$CH(CH_3)$—$CH_2$—;

linear copolymers comprising blocks of polydimethylsiloxane units and blocks of polyethylene glycol bis(2-methyl-2-propen-1-yl)ether monomers having the following structure (III)

where n=14 and which are terminated with 3-{3-[bis(2-hydroxypropyl)amino]-2-hydroxypropoxy]propyl groups, and mixtures of these aminated silicones.

The agent according to point 12, exemplified in that the at least one aminated silicone is contained in a total amount of from about 0.01 to about 5% by weight, preferably from about 0.1 to about 3% by weight, particularly preferably from about 0.5 to about 2% by weight, extremely preferably from about 1 to about 1.5% by weight, each based on the weight of the agent.

The agent according to one of the points 1-13, exemplified in that polyethylene glycol(s) with an average molecular weight of from about 100-100000 g·$Mol^{-1}$ are contained in a total amount of from about 0-0.2% by weight, preferably from about 0-0.1% by weight, each based on the weight of the agent.

The agent according to one of the points 1-14, exemplified in that fatty substances with a melting point of about 30° C. and above at 1013 mbar and a water solubility of about 0.005% by weight and below are contained in a total amount of from about 0-0.1% by weight, preferably 0% by weight, based on the weight of the agent.

A kit-of-parts packaging unit comprising—packed separately from each other
a) at least one container (C1) containing an agent for oxidative hair lightening or bleaching according to one of the points 1 to 15, and
b) at least one container (C2) containing an oxidizing agent preparation (M2), which contains from about 40-96% by weight, preferably from about 70-93% by weight, particularly preferably from about 80-90% by weight, water, furthermore hydrogen peroxide in a total amount of from about 0.5 to about 23% by weight, more preferably from about 2.5 to about 21% by weight, particularly preferably 4 to 20% by weight, very particularly preferably from about 5-18% by weight and extremely preferably from about 6-12% by weight, and has a pH value in the range from about 2.0 to about 6.5, preferably from about 2.5-5.5, particularly preferably from about 2.8 to about 5.0, in each case measured at about 20° C., the percentages by weight being based in each case on the weight of the oxidizing agent preparation (M2).

The packaging unit (kit-of-parts) according to point 16, exemplified in that the oxidant preparation (M2) contains at least one cationic surfactant, preferably in a total amount of from about 0.05-3% by weight, particularly preferably of from about 0.1-1.5% by weight, extremely preferably of from about 0.3-0.9% by weight, in each case based on the weight of the oxidant preparation (M2).

The kit-of-parts according to point 17, exemplified in that the oxidizer preparation (M2) does not contain a polymer with a degree of polymerization of at least about 200 and does not contain a polymer with a molecular weight of about 10,000 Dalton or higher.

The packaging unit (kit-of-parts) according to point 16, exemplified in that the oxidizing agent preparation (M2) contains at least one copolymer selected from crosslinked acrylic acid/acrylic acid-C1-C6-alkyl ester copolymers and crosslinked methacrylic acid/acrylic acid-C1-C6-alkyl ester copolymers, preferably in a total amount of from about 0.1-7% by weight, particularly preferably from about 0.5-6% by weight, extremely preferably from about 1-4.5% by weight, in each case based on the weight of the oxidizing agent preparation (M2), and preferably contains no cationic surfactant.

The kit-of-parts according to one of the points 16-19, exemplified in that the kit further comprises at least one container (C3) containing a, preferably powdery, blonde booster composition (M3) comprising at least one oxidizing agent selected from sodium percarbonates and inorganic salts of a peroxosulfuric acid and mixtures thereof, in a total amount of from about 5-100% by weight, preferably from about 10-98%, particularly preferably from about 25-70%, extremely preferably from about 30-50%, by weight, in each case based on the weight of the blond booster, and from 0 to about 8%, preferably from about 0.1 to about 5%, particularly preferably from about 0.5 to about 2.5%, by weight of water, in each case based on the weight of the blond booster.

The packaging unit (kit-of-parts) according to point 20, which is composed with respect to the weight ratio (M1):(M2):(M3) of the three components to one another in such a way that the weight ratio (M1):(M2) is in the range from about 1:0.8 to about 1:2.5, preferably from about 1:1 to about 1:2, and (M3) is present in an amount of from about 5-25 wt. %, preferably from about 7-20 wt. %, particularly preferably from about 7.5-17 wt. %, based on the weight of the total mixture of (M1), (M2) and (M3).

A process for oxidative hair lightening or bleaching, comprising the following process steps:
i) Provision of a cosmetic product for oxidative hair lightening or bleaching (M1) according to one of the points 1 to 15,
ii) Provision of an oxidizing agent preparation (M2), containing from about 40-96 wt. %, preferably from about 70-93 wt. %, particularly preferably from about 80-90 wt. %, water, furthermore hydrogen peroxide in a total amount of from about 0.5 to about 23 wt. %, more preferably from about 2.5 to about 21 wt. %, particularly preferably from about 4 to about 20 wt. %, very particularly preferably 5 to 18 wt. % and extremely preferably from about 6 to about 12 wt. %, and having a pH value in the range from about 2.0 to about 6.5, preferably from about 2.5-5.5, particularly preferably from about 2.8 to about 5.0, in each case measured at about 20° C., wherein the weight-% indications are each based on the weight of the oxidizing agent preparation (M2), optionally containing either at least one cationic surfactant or at least one copolymer selected from crosslinked acrylic acid/acrylic acid-C1-C6-alkyl ester copolymers and crosslinked methacrylic acid/acrylic acid-C1-C6-alkyl ester copolymers,
iii) Mixing of the cosmetic agent (M1) with the oxidizing agent preparation (M2), preferably in a weight ratio (M1):(M2) in the range of from about 1:0.8 to about 1:2.5, preferably from about 1:1 to about 1:2, immediately afterwards
iv) Apply the mixture obtained in step iii) to the hair and leaving this mixture on the hair for a time of from about 1 to about 60 minutes, preferably of from about 20 to about 45 minutes, at room temperature and/or at from about 30-60° C., preferably at from about 32-50° C.,
v) rinsing the hair with water and/or a cleansing composition, and
vi) if necessary, apply an after-treatment agent to the hair and rinse if necessary, followed by drying.

A process for oxidative hair lightening or bleaching according to point 20, exemplified in that the oxidizing agent preparation (M2) contains at least one cationic surfactant, preferably in a total amount of from about 0.05-3% by weight, particularly preferably of from about 0.1-1.5% by weight, extremely preferably from about 0.3-0.9% by weight, in each case based on the weight of the oxidant preparation (M2) and does not contain any polymer with a degree of polymerization of at least about 200 and no polymer with a molecular weight of about 10,000 Daltons or higher.

A process for oxidative hair lightening or bleaching according to point 20, exemplified in that the oxidizing agent preparation (M2) contains at least one copolymer selected from crosslinked acrylic acid/acrylic acid-C1-C6-alkyl ester copolymers and crosslinked methacrylic acid/acrylic acid-C1-C6-alkyl ester copolymers, preferably in a total amount of from about 0.1-7 wt. %, particularly preferably from about 0.5-6% by weight, extremely preferably from about 1-4.5% by weight, in each case based on the weight of the oxidizing agent preparation (M2), and preferably contains no cationic surfactant.

A process for oxidative hair lightening or bleaching according to one of the points 20 to 24, exemplified in that before mixing the individual components (M1) and (M2), a preferably powdery blonde booster composition (M3) is further provided, which contains at least one oxidizing agent selected from sodium percarbonates and inorganic salts of a peroxosulfuric acid and mixtures thereof, in a total amount of from about 5-100 wt. %, preferably from about 10-98%, particularly preferably from about 25-70%, extremely preferably from about 30-50%, by weight, in each case based on the weight of the blond booster, and from 0 to about 8%, preferably from about 0.1 to about 5%, particularly preferably from about 0.5 to about 2.5%, by weight of water, in each case based on the weight of the blond booster, then the cosmetic agent (M1) is mixed with the oxidizing agent preparation (M2) and with the blonde booster composition (M3), preferably in such a weight ratio (M1):(M2):(M3) that the weight ratio (M1):(M2) is in the range of from about 1:0.8 to about 1:2.5, preferably from about 1:1 to about 1:2, and (M3) is mixed in an amount of from about 5-25 wt.-%, preferably from about 7-20 wt. %, particularly preferably from about 7.5-17 wt. %, based on the weight of the total mixture of (M1), (M2) and (M3), immediately afterwards, the mixture thus obtained is applied to the hair and left on the hair for a period of from about 1 to about 60 minutes, preferably from about 20 to about 45 minutes, at room temperature and/or at from about 30-60° C., preferably at from about 32-50° C., immediately afterwards the hair is rinsed with water and/or a cleansing composition, and if necessary, an after-treatment agent is applied to the hair and rinsed out if necessary and then dried.

The following examples are intended to illustrate the subject matter of the present disclosure, without restricting it thereto.

EXAMPLES

TABLE 1

Cream gel for oxidative hair lightening or bleaching

| Ingredient | Sample weight (% by weight) |
|---|---|
| Monoethanolamine (2-aminoethan-1-ol) | 7.40 |
| Potassium hydroxide | 0.50 |
| Sodium polyacrylate | (Active content) 1.00 |
| Mineral oil | 0.70 |
| Trideceth-6 | 0.10 |
| Sodium laureth(2) sulphate | 0.90 |
| Bis-Cetearyl Amodimethicone | 1.00 |
| L-arginine | 0.30 |
| L-Lysine HCl | 0.10 |
| Etidronic acid | 0.10 |
| Succinic acid | 0.10 |
| CI 77007 (Ultramarines) | 0.20 |
| Perfume | 0.40 |
| Water | ad 100.00 |

*Sodium polyacrylate, pregelled in a water-in-mineral oil emulsion with trideceth-6 as emulsifier
Viscosity: 40,000 mPas (at 20° C. with Brookfield rotational viscometer, 4 min−1, spindle 5)

TABLE 2

Cream gel for oxidative hair lightening or bleaching

| Ingredient | Sample weight (% by weight) |
|---|---|
| Ammonium hydroxide | 3.90 |
| Ammonium sulphate | 3.00 |
| Potassium hydroxide | 0.50 |
| Sodium polyacrylate | (Active content) 1.00 |
| Mineral oil | 0.70 |
| Trideceth-6 | 0.10 |
| Sodium laureth(2) sulphate | 0.90 |
| Bis-Cetearyl Amodimethicone | 1.00 |
| L-arginine | 0.20 |
| L-Lysine HCl | 0.20 |

TABLE 2-continued

Cream gel for oxidative hair lightening or bleaching

| Ingredient | Sample weight (% by weight) |
|---|---|
| Etidronic acid | 0.10 |
| Succinic acid | 0.10 |
| CI 77007 (Ultramarines) | 0.20 |
| Perfume | 0.40 |
| Water | ad 100.00 |

*Sodium polyacrylate, pregelled in a water-in-mineral oil emulsion with trideceth-6 as emulsifier
Viscosity: 40,000 mPas (at 20° C. with Brookfield rotational viscometer, 4 min−1, spindle 5)

TABLE 3

Cream gel for oxidative hair lightening or bleaching

| Ingredient | Sample weight (% by weight) |
|---|---|
| Ammonium hydroxide | 3.90 |
| Ammonium sulphate | 3.00 |
| Monoethanolamine (2-aminoethan-1-ol) | 3.00 |
| Potassium hydroxide | 0.50 |
| Sodium polyacrylate | (Active content) 1.00 |
| Mineral oil | 0.70 |
| Trideceth-6 | 0.10 |
| Sodium laureth(2) sulphate | 0.90 |
| Bis-Cetearyl Amodimethicone | 1.00 |
| L-arginine | 0.20 |
| L-Lysine HCl | 0.20 |
| Etidronic acid | 0.10 |
| Succinic acid | 0.10 |
| CI 77007 (Ultramarines) | 0.20 |
| Perfume | 0.40 |
| Water | ad 100.00 |

*Sodium polyacrylate, pregelled in a water-in-mineral oil emulsion with trideceth-6 as emulsifier
Viscosity: 40,000 mPas, measured at 20° C. with Brookfield rotational viscometer, 4 min−1, spindle 5

TABLE 4

Cream gel for oxidative hair lightening or bleaching

| Ingredient | Sample weight (% by weight) |
|---|---|
| Monoethanolamine (2-aminoethan-1-ol) | 7.50 |
| Potassium hydroxide | 0.50 |
| Sodium polyacrylate | (Active content) 1.00 |
| Mineral oil | 0.70 |
| Trideceth-6 | 0.10 |
| Sodium laureth(2) sulphate | 0.90 |
| Bis-Cetearyl Amodimethicone | 1.00 |
| Etidronic acid | 0.10 |
| CI 77007 (Ultramarines) | 0.20 |
| Perfume | 0.40 |
| Water | ad 100.00 |

*Sodium polyacrylate, pregelled in a water-in-mineral oil emulsion with trideceth-6 as emulsifier
Viscosity: 45,000 mPas, measured at 20° C. with Brookfield rotational viscometer, 4 min−1, spindle 5

TABLE 5

Cream gel for oxidative hair lightening or bleaching

| Ingredient | Sample weight (% by weight) |
|---|---|
| Ammonium hydroxide | 3.90 |
| Ammonium sulphate | 0.50 |
| Sodium polyacrylate | (Active content) 1.00 |
| Mineral oil | 0.70 |

TABLE 5-continued

Cream gel for oxidative hair lightening or bleaching

| Ingredient | Sample weight (% by weight) |
| --- | --- |
| Trideceth-6 | 0.10 |
| Sodium laureth(2) sulphate | 0.90 |
| Bis-Cetearyl Amodimethicone | 1.00 |
| Etidronic acid | 0.10 |
| CI 77007 (Ultramarines) | 0.20 |
| Perfume | 0.40 |
| Water | ad 100.00 |

*Sodium polyacrylate, pregelled in a water-in-mineral oil emulsion with trideceth-6 as emulsifier
Viscosity: 45,000 mPas, measured at 20° C. with Brookfield rotational viscometer, 4 min$^{-1}$, spindle 5

TABLE 6

Cream gel for oxidative hair lightening or bleaching

| Ingredient | Sample weight (% by weight) |
| --- | --- |
| Ammonium hydroxide | 3.90 |
| Ammonium sulphate | 3.00 |
| Monoethanolamine (2-aminoethan-1-ol) | 3.00 |
| Potassium hydroxide | 0.50 |
| Sodium polyacrylate | (Active content) 1.00 |
| Mineral oil | 0.70 |
| Trideceth-6 | 0.10 |
| Sodium laureth(2) sulphate | 0.90 |
| Bis-Cetearyl Amodimethicone | 1.00 |
| Etidronic acid | 0.10 |
| CI 77007 (Ultramarines) | 0.20 |
| Perfume | 0.40 |
| Water | ad 100.00 |

*Sodium polyacrylate, pregelled in a water-in-mineral oil emulsion with trideceth-6 as emulsifier
Viscosity: 45,000 mPas, measured at 20° C. with Brookfield rotational viscometer, 4 min$^{-1}$, spindle 5

TABLE 7

Oxidizing agent containing developer for whitening cream gels from tables 1 to 6

| Ingredient | Sample weight (% by weight) |
| --- | --- |
| Sodium benzoate | 0.04 |
| Dipicolinic acid (2,6-dicarboxypyridine) | 0.10 |
| Disodium pyrophosphate | 0.10 |
| Potassium hydroxide | 0.10 |
| 1.2-propanediol | 1.00 |
| Etidronic acid | 0.15 |
| Paraffin oil | 0.30 |
| Stearyl trimethylammonium chloride | 0.30 |
| Cetearyl alcohol | 3.40 |
| Ceteareth-20 | 1.00 |
| Hydrogen peroxide | 12.00 |
| Water | ad 100.00 |

Viscosity: 4,500 mPas, measured at 20° C. with a Haake VT 550 rotational viscometer at a rotation frequency of 4 min−1 with measuring geometry MV II

TABLE 8

Oxidizing agent containing developer for whitening cream gels from tables 1 to 6

| Ingredient | Sample weight (% by weight) |
| --- | --- |
| Isopropyl myristate | 10.00 |
| Cetearyl alcohol | 3.40 |
| Beeswax | 0.40 |
| Ceteareth-20 | 0.50 |
| PEG-40 Castor Oil | 0.85 |

TABLE 8-continued

Oxidizing agent containing developer for whitening cream gels from tables 1 to 6

| Ingredient | Sample weight (% by weight) |
| --- | --- |
| Dipicolinic acid (2,6-dicarboxypyridine) | 0.10 |
| Disodium pyrophosphate | 0.10 |
| Potassium hydroxide | 0.12 |
| Etidronic acid | 0.15 |
| Sodium cetaryl sulphate | 0.40 |
| Hydrogen peroxide | 11.50 |
| Water | ad 100.00 |

Viscosity: 3500 to 5000 mPas, measured at 20° C. with a Haake VT 550 rotational viscometer at a rotation frequency of 4 min$^{-1}$ with measuring geometry MV II

TABLE 9

Oxidizing agent containing developer for whitening cream gels from tables 1 to 6

| Ingredient | Sample weight (% by weight) |
| --- | --- |
| Sodium hydroxide | 0.40 |
| Dipicolinic acid (2,6-dicarboxypyridine) | 0.10 |
| Disodium pyrophosphate | 0.03 |
| Etidronic acid | 0.15 |
| Mixture of crosslinked (meth)acrylic acid/acrylic acid-C1-C6-alkyl ester copolymers (ex Aculyn 33A) | 4.20 |
| Sodium laureth(2) sulphate | 0.50 |
| Hydrogen peroxide | 12.00 |
| Water | ad 100.00 |

* Aculyn 33A: aqueous dispersion of acrylate copolymer (mixture of crosslinked (meth)acrylic acid/acrylic acid-C1-C6-alkyl ester copolymers); 28% by weight polymer content (active substance)
Viscosity: 200 mPas, measured at 20° C. with a Brookfield rotational viscometer at a rotation frequency of 20 min$^{-1}$ with spindle 2

TABLE 10

Blond Booster 1

| Ingredient | Sample weight (% by weight) |
| --- | --- |
| Potassium persulphate | 97.0 |
| Silica | 2.5 |
| Potassium sulphate | 0.5 |

TABLE 11

Blond Booster 2

| Ingredient | Sample weight (% by weight) |
| --- | --- |
| Potassium persulphate | 42.0 |
| Sodium silicate with a molar SiO$_2$/Na$_2$O ratio of 2.67 | 23.0 |
| Sodium persulphate | 16.0 |
| Ammonium persulphate | 12.0 |
| Water | 4.8 |
| Silica | 1.0 |
| Disodium EDTA | 0.6 |
| Potassium sulphate | 0.2 |
| Ammonium sulphate | 0.2 |
| Sodium sulphate | 0.2 |

Preparation of the Application Mixtures and Lightening of the Hair

One whitening cream gel each according to one of Tables 1 to 6 and one of the developers according to Table 7 or Table 8, each in equal parts by weight, were homogeneously mixed together with the addition of a blonde booster according to Table 10 or Table 11. The application mixtures thus obtained were applied to strands of human hair (brown hair, Fischbach & Miller company) immediately after production (liquor ratio 4 grams of application mixture per gram of hair) and left on the hair for 45 minutes at 35° C. in a drying cabinet. The strands were then rinsed out and dried with a hairdryer.

TABLE 12

Preparation of the application mixtures for the lightening of hair

| Brightening gel (M1) (described product) | Developer (M2) | Blond booster (M3) | Weight ratio (M1):(M2):(M3) | Viscosity range of the application mixture [mPas]* |
|---|---|---|---|---|
| according to Table 1 | according to Table 7 | according to Table 10 | 60:60:10** | 17,000-20,000 |
| according to Table 1 | according to Table 8 | according to Table 10 | 60:60:10 | 17,000-20,000 |
| according to Table 2 | according to Table 7 | according to Table 11 | 50:50:20 | 17,000-20,000 |
| according to Table 2 | according to Table 8 | according to Table 11 | 50:50:20 | 17,000-20,000 |
| according to Table 3 | according to Table 7 | according to Table 11 | 50:50:20 | 17,000-20,000 |
| according to Table 3 | according to Table 8 | according to Table 11 | 50:50:20 | 17,000-20,000 |
| according to Table 4 | according to Table 7 | according to Table 10 | 60:60:10 | 17,000-20,000 |
| according to Table 4 | according to Table 8 | according to Table 10 | 60:60:10 | 17,000-20,000 |
| according to Table 5 | according to Table 7 | according to Table 11 | 50:50:20 | 17,000-20,000 |
| according to Table 5 | according to Table 8 | according to Table 11 | 50:50:20 | 17,000-20,000 |
| according to Table 6 | according to Table 7 | according to Table 11 | 50:50:20 | 17,000-20,000 |
| according to Table 6 | according to Table 8 | according to Table 11 | 50:50:20 | 17,000-20,000 |

*Viscosity: measured at 20° C. with a Brookfield rotational viscometer at a rotation frequency of 4 min$^{-1}$ with spindle 5
**Proportion of component (M3) in the weight of the total mixture of (M1), (M2) and (M3): 7.69% by weight
*** Proportion of component (M3) in the weight of the total mixture of (M1), (M2) and (M3): 16.67% by weight While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for oxidative hair lightening or bleaching, comprising, in each case based on a weight of the agent;
   from 70 to about 95% by weight water,
   an alkalising agent,
   a surfactant selected from anionic, zwitterionic and amphoteric surfactants and mixtures thereof, wherein the surfactant is present in the agent in a total amount of from about 0.1 to about 2% by weight,
   sodium polyacrylate in a total amount of from about 0.1 to about 1.5% by weight, wherein the sodium polyacrylate has a mass-average molar mass Mw in the range from 1,000,000 to 20,000,000 Daltons,
   a linear saturated alkanol comprising two or three hydroxy groups and 2 to 8 carbon atoms in the alkyl group, wherein the linear saturated alkanol is present in the agent in a total amount of from about 0 to about 3% by weight,
   where the agent comprises;
   no crosslinked copolymer formed from acrylic acid and non-ethoxylated esters of acrylic acid with linear C10-C30 monoalcohols as monomers,
   no saturated or unsaturated non-alkoxylated alkanols having a hydroxy group and 1 to 50 carbon atoms in the alk(en)yl group,
   no saturated or unsaturated alkanecarboxylic acids with 1 to 50 carbon atoms, and
   no oxidizing agents,
   wherein the agent has a pH value in the range of from about 10.0 to about 11.0, measured at 20° C.

2. The agent according to claim 1, wherein the alkalizing agent is selected from the group of ammonium hydroxide, basic amino acids, alkali metal hydroxides, alkanolamines, alkali metal silicates, alkali metal phosphates, alkali metal hydrogen phosphates, and mixtures thereof.

3. The agent according to claim 1, wherein the surfactant is selected from $C_8$-$C_{20}$ alkyl sulphates, $C_8$-$C_{20}$ alkyl ether sulphates, and $C_8$-$C_{20}$-ether carboxylic acids, each with 8 to 20 C atoms in the alkyl group and 0 to 12 ethylene oxide groups in the molecule, cocoacylaminopropyl dimethylammonium glycinate, and from mixtures of these surfactants.

4. The agent according to claim 1, wherein the sodium polyacrylate is provided as pregelled in a water-in-oil emulsion, such that the agent further comprises an oil and a non-ionic surfactant.

5. The agent according to claim 1, wherein the agent has a viscosity in the range from about 2,000 to about 70,000 mPas, measured at about 20° C. with a Brookfield rotational viscometer at a rotational frequency of about 4 min$^{-1}$ with spindle 5.

6. The agent according to claim 1, wherein the alkalizing agent is selected from ammonium hydroxide, basic amino acids, alkali metal hydroxides, alkanolamines, alkali metal silicates, alkali metal phosphates, alkali metal hydrogen phosphates, and mixtures thereof, wherein the alkalizing agent is present in the agent in an amount of from about 2 to about 10% by weight, based on the weight of the agent.

7. The agent according to claim 1, wherein the agent further comprises an aminated silicone selected from;
Compounds of structural formula (I)

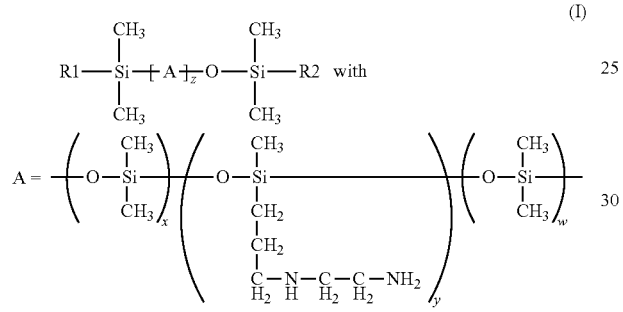

wherein
 i. x and y stand independently for numbers from 1 to about 100,
 ii. w stands for a number from 0 to about 100,
 iii. z is a number from 1 to about 100, whereby, if z≥2, the respective values x, y and w in a structural element A can each be selected independently of preceding structural elements A
 and
 iv. R1 and R2 independently of one another represent a linear or branched, saturated, unsaturated or polyunsaturated $C_5$-$C_{20}$ alkyl group, a hydroxy group, a $C_1$-$C_{30}$ alkoxy group, a carboxy-$C_1$-$C_{30}$ alkyl group or a $C_1$-$C_6$ alkyl-(O—$CH_2$—$CH_2$)$_n$—O— group, wherein n is an integer from 1 to about 60;
Compounds of structural formula (II),

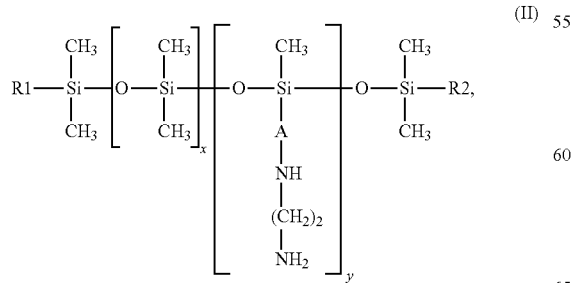

wherein
 i. x and y independently of one another stand for numbers from 1 to about 5000,
 ii. R1 and R2 independently represent a methyl group or a hydroxy group, and
 iii. A represents a linear or branched alkylene group with 2 to 8 carbon atoms,
linear copolymers comprising blocks of polydimethylsiloxane units and blocks of polyethylene glycol bis(2-methyl-2-propen-1-yl)ether monomers having the following structure (III)

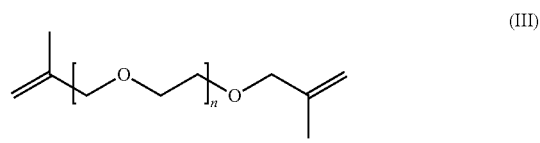

where n=14 and are terminated with 3-{3-[bis(2-hydroxypropyl)amino]-2-hydroxypropoxy]propyl groups, and mixtures of these aminated silicones.

8. A kit-of-parts packaging unit comprising—packed separately from each other—
 a) at least one container (C1) comprising an agent for oxidative hair lightening or bleaching according to claim 1, and
 b) at least one container (C2) comprising an oxidizing agent preparation (M2), which comprises from about 40 to about 96% by weight water, hydrogen peroxide in a total amount of from about 0.5 to about 23% by weight, and has a pH value in the range from about 2.0 to about 6.5, measured at about 20° C., the percentages by weight being based in each case on a weight of the oxidant preparation (M2).

9. The kit-of-parts according to claim 8, wherein the oxidant preparation (M2) comprises at least one cationic surfactant, wherein the at least one cationic surfactant is present in the oxidant preparation (M2) in a total amount of about 0.05 to about 3% by weight, based on the weight of the oxidant preparation (M2).

10. The kit-of-parts according to claim 9, wherein the oxidizing agent preparation (M2) does not comprise a polymer having a degree of polymerization of at least about 200 and the oxidizing agent preparation (M2) does not comprise a polymer having a molecular weight of about 10,000 Daltons or higher.

11. The kit-of-parts according to claim 8, wherein the kit-of-parts further comprises at least one container (C3) comprising a blonde booster composition (M3), wherein the blonde booster composition (M3) comprises at least one oxidizing agent selected from sodium percarbonates, inorganic salts of a peroxosulfuric acid, and mixtures thereof, in a total amount of from about 5 to about 100 wt. %, based on a weight of the blond booster composition (M3), and from 0 to about 8% by weight of water, based on the weight of the blond booster composition (M3).

12. A method for oxidative lightening or bleaching of hair, the method comprising the steps of:
 i) providing an agent (M1) for oxidative hair lightening or bleaching according to claim 1, ii) providing an oxidizing agent preparation (M2), comprising;
  from about 40 to about 96 wt. % water, based on a weight of the oxidizing agent preparation (M2), hydrogen peroxide in a total amount of from about 0.5 to about 23 wt. %, based on the weight of the oxidizing agent preparation, and having a pH value in the range from about 2.0 to about 6.5, measured at about 20° C., optionally comprising either at least one cationic surfactant or at least one copolymer selected from crosslinked acrylic acid/acrylic acid-C1-C6-alkyl ester copolymers and crosslinked methacrylic acid/acrylic acid-C1-C6-alkyl ester copolymers, iii) mixing the agent (M1) with the oxidizing agent preparation (M2) in a weight ratio (M1):(M2) in a range of from about 1:0.8 to about 1:2.5 to form a mixture, and immediately afterwards iv) applying the mixture obtained in step iii) to the hair and leaving the mixture on the hair for a time of from about 1 to about 60 minutes, at room temperature or at from about 30 to about 60° C., v) rinsing the hair with water and/or a cleansing composition, and vi) if necessary, applying an after-treatment agent to the hair and rinsing the hair if necessary, followed by drying.

13. The method for oxidative lightening or bleaching the hair according to claim 12, wherein the oxidizing agent preparation (M2) comprises at least one cationic surfactant in a total amount of from about 0.05 to about 3% by weight, based on the weight of the oxidant preparation (M2), and the oxidizing agent preparation (M2) does not comprise any polymer with a degree of polymerization of at least about 200 and the oxidizing agent preparation (M2) comprises no polymer with a molecular weight of about 10,000 Daltons or higher.

14. The method for oxidative lightening or bleaching the hair according to claim 12, further comprising:

Providing a blonde booster composition (M3), wherein the blonde booster composition (M3) is powdery, wherein the blonde booster composition (M3) comprises an oxidizing agent selected from sodium percarbonates, inorganic salts of a peroxosulfuric acid, and mixtures thereof in a total amount of from about 5 to about 100 wt. %, based on the weight of the blond booster composition (M3), and comprising from 0 to about 8% water, based on a weight of the blonde booster composition (M3), and wherein mixing the cosmetic agent (M1) with the oxidizing agent preparation (M2) in step iii) further comprises mixing the cosmetic agent (M1) with the oxidizing agent preparation (M2) and with the blonde booster composition (M3), in such a weight ratio (M1):(M2):(M3) that the weight ratio (M1):(M2) is in the range of from about 1:0.8 to about 1:2.5, and (M3) is mixed in an amount of from about 5-25 wt. %, based on a weight of the total mixture of (M1), (M2) and (M3).

15. The method for oxidative lightening or bleaching the hair according to claim 12, wherein the oxidizing agent preparation (M2) comprises:

at least one surfactant selected from anionic surfactants and non-ionic surfactants and mixtures thereof in a total amount of from about 0.05 to about 2 wt. %, at least one linear, saturated 1-alkanol having 14 to 22 carbon atoms, selected from 1-tetradecanol, 1-hexadecanol, 1-octadecanol and 1-eicosanol and mixtures thereof, in a total amount of from about 1 to about 5% by weight, optionally at least one oil in a total amount of from about 0.2 to about 50% by weight, and optionally at least one cationic surfactant in a total amount of from about 0.05 to about 3% by weight, where all quantities refer to the weight of the oxidizing agent preparation (M2).

16. The agent according to claim 1, wherein the agent has a viscosity in the range from about 10,000 to about 60,000 mPas, measured at about 20° C. with a Brookfield rotational viscometer at a rotational frequency of about 4 min$^{-1}$ with spindle 5.

17. The agent according to claim 1, wherein the agent has a viscosity in the range from about 20,000 to about 50,000 mPas, measured at about 20° C. with a Brookfield rotational viscometer at a rotational frequency of about 4 min$^{-1}$ with spindle 5.

18. The agent according to claim 1, wherein the agent has a viscosity in the range from about 35,000 to about 45,000 mPas, measured at about 20° C. with a Brookfield rotational viscometer at a rotational frequency of about 4 min$^{-1}$ with spindle 5.

19. The agent according to claim 1, wherein the alkalizing agent is present in the agent in an amount of from about 3 to about 9 weight percent, based on the total weight of the agent.

20. The agent according to claim 1, wherein the alkalizing agent is present in the agent in an amount of from about 4.5 to about 7 weight percent, based on the total weight of the agent.

* * * * *